US009101720B2

(12) United States Patent
Okihara et al.

(10) Patent No.: US 9,101,720 B2
(45) Date of Patent: Aug. 11, 2015

(54) PREFILLED SYRINGE

(75) Inventors: Hitoshi Okihara, Shizuoka-ken (JP);
Hideo Watanabe, Shizuoka-ken (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 335 days.

(21) Appl. No.: 13/434,919

(22) Filed: Mar. 30, 2012

(65) Prior Publication Data

US 2012/0184920 A1    Jul. 19, 2012

Related U.S. Application Data

(63) Continuation of application No. PCT/JP2010/067076, filed on Sep. 30, 2010.

(30) Foreign Application Priority Data

| Sep. 30, 2009 | (JP) | 2009-228758 |
| Feb. 8, 2010 | (JP) | 2010-025996 |

(51) Int. Cl.
*A61M 5/31* (2006.01)
*A61M 5/315* (2006.01)
*A61M 5/145* (2006.01)

(52) U.S. Cl.
CPC ......... *A61M 5/31515* (2013.01); *A61M 5/1452* (2013.01); *A61M 5/1458* (2013.01)

(58) Field of Classification Search
CPC ............ A61M 5/513; A61M 5/31515; A61M 5/31511; A61M 5/1452; A61M 5/1458
USPC ......... 604/187, 211, 218, 219, 220, 221, 222, 604/228, 229
See application file for complete search history.

(56) References Cited

U.S. PATENT DOCUMENTS 5,489,266 A * 2/1996 Grimard ........................ 604/89
2005/0240159 A1 * 10/2005 Kito et al. .................... 604/222

(Continued)

FOREIGN PATENT DOCUMENTS

| CN | 1152882 A | 6/1997 |
| JP | 6-39005 U | 5/1994 |

(Continued)

OTHER PUBLICATIONS

International Search Report (PCT/ISA/210) issued on Dec. 28, 2010, by Japanese Patent Office as the International Searching Authority for International Application No. PCT/JP2010/067076.

(Continued)

*Primary Examiner* — Aarti B Berdichevsky
*Assistant Examiner* — Bradley Osinski
(74) *Attorney, Agent, or Firm* — Buchanan Ingersoll & Rooney PC

(57) ABSTRACT

A prefilled syringe has a gasket composed of a gasket body and a plunger-mounting member mounted. The plunger-mounting member has a distal part, spiral ribs formed on an outer surface of the distal part, a flange part, and a plunger-mounting part formed on an inner surface of a hollow part. The gasket body has a spiral screwing part which screws the spiral ribs and an accommodation part for accommodating a portion where the spiral ribs are formed. A plunger has a mounting distal part. The plunger-mounting part has a spiral concave portion and an engaging rib disposed at a side distal from the spiral concave portion. The mounting distal part of the plunger has a spiral projected portion capable of screwing the spiral concave portion and an engaging portion which engages the engaging rib of the plunger-mounting member.

10 Claims, 32 Drawing Sheets

(56) References Cited

U.S. PATENT DOCUMENTS

2008/0097337 A1* 4/2008 Judd et al. .................. 604/198
2011/0178475 A1   7/2011 Tanaka et al.

FOREIGN PATENT DOCUMENTS

| JP | 2002-272843 A | 9/2002 |
| JP | 3665646 B2 | 6/2005 |
| JP | 2007-44159 A | 2/2007 |
| JP | 2007-202822 A | 8/2007 |
| JP | 2008-307237 A | 12/2008 |
| JP | 2009-142508 A | 7/2009 |
| WO | 95/30444 A1 | 11/1995 |
| WO | WO 01/97885 A1 | 12/2001 |
| WO | WO 2007/015469 A1 | 2/2007 |

OTHER PUBLICATIONS

Extended European Search Report dated Jun. 24, 2013, issued by the European Patent Office in the corresponding European Application No. 10820637.6. (4 pages).

First Office Action and Search Report issued on Jul. 31, 2013, by the Chinese Patent Office in corresponding Chinese Patent Application No. 201080054294.6. (5 pages).

* cited by examiner

PREFILLED SYRINGE

CROSS REFERENCES TO RELATED APPLICATION(S)

This application is a continuation of International Application No PCT/JP 2010/067076 filed on Sep. 30, 2010, and claims priority to Japanese Patent Application No. 2009-228758 filed on Sep. 30, 2009 and Japanese Patent Application No. 2010-025996 filed on Feb. 8, 2010, the entire content of both of which is incorporated herein by reference.

TECHNICAL FIELD

The present invention relates to a prefilled syringe in which a medicine is filled in advance.

BACKGROUND DISCUSSION

Many syringes are conventionally used. Recently there are many cases in which syringes are used by mounting them on syringe pumps respectively. Many prefilled syringes in which a medicine is filled in advance are utilized in recent years. There is a case in which the prefilled syringe is used by mounting it on the syringe pump.

In inserting the gasket into the prefilled syringe, generally used is a method so-called a vacuum plugging in which after a medicine is filled inside the outer cylinder whose opening formed at its distal end is sealed, the gasket is disposed at an opening of the outer cylinder under a pressure-decreased atmosphere (under a vacuum atmosphere), and thereafter a normal pressure state is generated to insert the gasket into the outer cylinder. In a state in which the plunger has been mounted on the gasket, it is difficult to dispose the gasket at the opening of the outer cylinder. Thus a vacuum plugging work is performed without mounting the plunger on the gasket. Therefore generally the prefilled syringe necessitates a plunger-mounting work to be performed subsequently. To make it easy to perform the work of mounting the plunger on the gasket, prevent liquid from leaking in mounting the plunger on the gasket, and decrease the amount of the work of restraining the rise of an internal pressure, generally the prefilled syringe has a mounting mechanism of mounting the plunger on the gasket by screwing a male screw portion formed on the plunger on a female screw portion formed on the gasket.

As described above, there are cases in which a medicine is given to a patient by using the syringe or the prefilled syringe by mounting them on the syringe pump. In the case where the syringe pump is used, continuous dosing of a very small amount of the medicine is performed. When the syringe pump is placed at a position higher than the patient, there is a possibility of the occurrence of a phenomenon in which the medicine is rapidly administered to the patient owing to a fall. That is, in such a state, a negative pressure is generated inside the syringe owing to the fall, and thus the gasket is sucked to the front side of the outer cylinder. The continuous dosing of a very small amount of the medicine is accomplished while a means for pressing the syringe pump fixed to the plunger is preventing the movement of the gasket caused by the sucking. When the negative pressure overcomes the engaging force acting between the plunger and the gasket, there is a danger that the gasket separates from the plunger. When the gasket separates from the plunger, the medicine inside the syringe is rapidly administered to the patient.

As syringes having a mechanism of preventing the separation of the gasket from the plunger, Japanese Patent Application Laid-Open No. 2002-272843 (patent document 1), Japanese Patent Application Laid-Open No. 2009-142508 (patent document 2), International Publication WO01-97885 (patent document 3), and Japanese Patent Application Laid-Open No. 2007-202822 (patent document 4) are listed. The patent documents 1 through 3 are proposed by the present applicant.

Syringes in which the gasket is constructed of a gasket body and a plunger-mounting member are proposed. As such syringes, for example, Japanese Utility Model Application Laid-Open No. 6-39005 (patent document 5), Japanese Patent Application Laid-Open No. 2007-44159 (patent document 6), Japanese Patent Application Laid-Open No. 2008-307237 (patent document 7), and Japanese Patent No. 3665646 (patent document 8, WO95-30444) are listed.

A syringe 1 of the patent document 1 (Japanese Patent Application Laid-Open No. 2002-272843) has an outer cylinder 2, a gasket 3 capable of sliding inside the outer cylinder 2, and a plunger 4, having the function of perform the operation of moving the gasket 3, which is inserted into the outer cylinder 2 from the opening formed at the proximal end thereof. The liquid 7 is liquid-tightly accommodated in advance inside the space surrounded with the outer cylinder 2 and the gasket 3. The flange 44 is formed at the head part 43 formed at the distal portion of the plunger 4. The gasket 3 has the hollow part. The screw thread 34 is formed on the inner surface of the proximal side of the hollow part. The space 35 for accommodating the flange 44 is formed at a portion located distally from the screw thread 34. The flange 44 which has entered the space 35 across the screw thread 34 engages the space 35 in a loosely engage state.

In this syringe, the flange 44 formed at the head part 43 of the distal portion of the plunger 4 is not screwlike. Thus when a medicine is administered to a patient by the syringe mounted on the syringe pump with the syringe pump placed at a position higher than the patient, there is a fear that the plunger separates from the gasket.

The syringe 10 of the patent document 2 (Japanese Patent Application Laid-Open No. 2009-142508) has the gasket 3, the outer cylinder 2, and the plunger 4. The plunger 4 has the spiral rib 44 formed on the outer surface of the head part 42. The gasket 3 has the spiral screwing part 33 which is to screw the spiral rib 44, the annular rib 34, for preventing the separation of the plunger from the gasket, which is located at a position in the vicinity of the spiral screwing part 33 and distal therefrom, and the accommodation part 32 for accommodating the portion where the spiral rib 44 of the head part 42 of the plunger is formed. The annular rib 34 has the rib-absent portion 35 for guiding the spiral rib 44 which has reached the annular rib owing to the progress of the screwing between the spiral rib 44 of the plunger and the spiral screwing part 33 of the gasket to the accommodation part.

This syringe is effective for preventing the separation of the plunger from the gasket. But in dependence on a manner of the work of mounting the plunger on the gasket, defective mounting of the plunger on the gasket sometimes occurs.

In the patent document 3 (International Publication WO01-97885), at the distal portion of the plunger 4, the head part (coupling portion) 43 to be inserted into the hollow part 33 of the gasket 3 and coupled to the gasket 3 is formed. A male screw 51 is formed on the outer circumferential surface of the head part 43. The female screw 52 on which the male screw 51 can be screwed is formed on the inner circumferential surface of the hollow part 33 of the gasket 3. The head part 43 has the elastic piece 61 located at a position distal from the male screw 51 and the projected portions 62, projectingly formed toward the outer circumference thereof, which are located in the vicinity of the end portions of elastic pieces 61. The ring-shaped engaging projected part 63 is formed on the inner circumferential surface of the hollow part 33 of the gasket 3 at a position distal from the female screw 52.

In this syringe, the plunger is mounted on the gasket by rotating the plunger. Thus it is necessary to perform the operation of rotating the plunger to mount the plunger on the gasket. There is a case in which a screwing operation is not properly performed. In this state, there is a possibility that the outer side surface of the gasket is not a perfect circle and thus a liquid may leak. Further a stress generated when the plunger mounted on the gasket is inclined is directly transmitted to the gasket and the liquid may leak.

The plunger used for the syringe of the patent document 4 (Japanese Patent Application Laid-Open No. 2007-202822) includes the plunger rod 22 and the gasket 21. The gasket 21 has the inner space whose distal end is closed and has an opening 212, having a smaller diameter than that of the inner space, which is formed at the proximal end thereof. The male screw-shaped projected part 223 is formed at the distal end of the plunger rod 22. When the projected part 223 enters the inner space across the opening 212, the gasket 21 and the plunger rod 22 engage each other in a free fit-on state.

The "opening having a smaller diameter" of the syringe is "not screwlike", and necessarily has the function of preventing the plunger from dropping when the plunger is rotated reversely and in addition preventing the plunger from dropping when the plunger is pulled toward the proximal end of the syringe. Therefore the "opening having a smaller diameter" is required to have a high strength. Thus when improper screwing occurs between the projected part 223 of the plunger rod 22 and the convexity of the female screw of the gasket, the convexity screws the projected portion 223 with the convexity being twisted. As a result, the circularity of the peripheral side surface of the gasket becomes low and there is a possibility that a liquid may leak.

In the patent document 5 (Japanese Utility Model Application Laid-Open No. 6-39005), the reinforcing material 30 made of synthetic resin is fitted on the inner chamber portion of the plunger 20 closely fitted in the syringe 2 serving as a container. The reinforcing material 30 reinforces the peripheral wall portion 23 forming the inner chamber portion of the plunger 20. The plunger rod 10 is removably mounted on the reinforcing material 30. The insertion portion 16 of the plunger rod 10 is inserted into the insertion hole 34 (see FIG. 2 of the specification of the patent document 5) of the cover portion 32 of the reinforcing material 30. The plunger rod 10 is rotated to fit the opposed side 18 of the window spline 17 of the insertion portion 16 of the plunger rod 10 on the fit-on groove 36 (see FIG. 3 of the specification of the patent document 5) of the back surface 35 of the cover portion 32 of the reinforcing material 30. Thereby the mounting of the plunger rod 10 on the plunger 20 on which the reinforcing material 30 has been mounted finishes.

In this syringe, at the time the plunger-mounting work is performed, it is necessary to fit the window spline on the slit-like fit-on groove and in addition, the plunger 20 is invisible because the plunger rod stands in the way. Thus it is not easy to perform the mounting work. In addition, after the mounting work finishes, there is a danger that when the window spline is fitted on the fit-on groove, the plunger rod easily separates from the plunger.

The syringe 1 of the patent document 6 (Japanese Patent Application Laid-Open No. 2007-44159) has the outer cylinder 2, the gasket 3 capable of sliding inside the outer cylinder 2, and the plunger 4 for performing the operation of moving the gasket 3. The gasket 3 and the plunger 4 are coupled to each other by a coupling mechanism. The plunger 4 is composed of the upper plunger 41 and the lower plunger 42 fitted thereon. At the time of fitting the lower plunger 41 on the upper plunger 42, the convex portion 422 formed on the lower plunger 42 is inserted into the concave portion 412 formed on the upper plunger 41. When the convex portion 422 is inserted deep into the concave portion 412, the lower plunger 42 is rotated until the convex portion 422 formed on the lower plunger 42 is positioned at the end of the concave portion 412 formed on the upper plunger 41. At this time, the upper plunger 41 and the lower plunger 42 are engaged each other in a loosely engage state by providing the gap at the engaging portion where the upper plunger 41 and the lower plunger 42 engage each other. This syringe also necessitates a rotation operation to be performed to mount the plunger on the gasket.

In the prefilled syringe of the patent document 7 (Japanese Patent Application Laid-Open No. 2008-307237), a medicinal solution is filled therein and the gasket is plugged into the outer cylinder. The prefilled syringe includes the coupler which screws the proximal end of the gasket, the bottom rod coupled to the coupler at its proximal end, the stopper formed on the coupler, and the engaging part, formed on the bottom rod, which engages the stopper owing to the rotation of the bottom rod in the screwing direction. When the stopper contacts the engaging portion in the direction opposite to the screwing direction, the stopper elastically deforms and does not engage the engaging part.

Similarly to the syringe of the patent document 6, in this syringe, it is not easy to perform a mounting work.

The syringe of the patent document 8 (Japanese Patent No. 3665646: WO95-30444) shown in FIGS. 1 through 6 of the specification thereof has the barrel, the plunger, and the plunger rod. By driving the plunger rod, the plunger generates an axial tensile force. As a result, the diameter of the plunger decreases. With the friction between the inside of the barrel and the plunger being decreased owing to the contraction of the diameter of the plunger, the elongation of the plunger is so restricted that the sealing between the inside of the barrel and the plunger is maintained. The plunger rod has the rod member and the connection member for the plunger. The rod member is axially slidable with respect to the connection member. In the syringe of the embodiment shown in FIGS. 1 through 6 of the specification of the patent document 8, the plunger insertion part 68 has the female screw 69 which engages the male screw 71 of the plunger rod 50. The plunger rod 50 has the male screw 71 so designed that the male screw 71 engages the female screw 69 of the plunger insertion part 68. This syringe also necessitates a rotation operation to be performed to mount the plunger. The syringe of the embodiment shown in FIGS. 7 through 18 of the specification of the patent document 8 has the semicircular plunger rod distal end 164 having the convex surface projected toward the plunger. It is necessary to insert the distal end 164 into the cross-shaped slit shown in FIG. 18 and thereafter rotate the plunger. In this syringe, to mount the plunger on the plunger rod, it is necessary to perform the work placing the distal end 164 in position and inserting the distal end 164 into the slit and the operation of rotating the plunger. As shown in FIG. 11, because the distal end 164 contacts and deforms the plunger (gasket, there is a high possibility that a liquid leaks.

Similarly to the syringes of the patent documents 6 and 7, in this syringe, it is not easy to perform the mounting work and in addition there is a danger that after the plunger rod is mounted on the plunger, the plunger rod may separate from the plunger.

PRIOR ART DOCUMENT

Patent Document

Patent document 1: Japanese Patent Application Laid-Open No. 2002-272843
Patent document 2: Japanese Patent Application Laid-Open No. 2009-142508
Patent document 3: International Publication WO01-97885 (patent document 3)
Patent document 4: Japanese Patent Application Laid-Open No. 2007-202822
Patent document 5: Japanese Utility Model Application Laid-Open No. 6-39005
Patent document 6: Japanese Patent Application Laid-Open No. 2007-44159
Patent document 7: Japanese Patent Application Laid-Open No. 2008-307237
Patent document 8: Japanese Patent No. 3665646 (WO95-30444)

SUMMARY

Therefore it is an object of the present invention to provide a prefilled syringe which allows an operator to confirm that a plunger has been mounted on a gasket during a work of mounting the plunger on the gasket, is capable of securely restraining the gasket mounted on the plunger from being removed therefrom, and is unlikely to deform the gasket, even though the plunger inclines.

The prefilled syringe which achieves the above-described objects is as described below.

A prefilled syringe of this invention comprises a prefilled syringe body including an outer cylinder possessing an opening at a distal end of the outer cylinder, a gasket slidably accommodated inside the outer cylinder, a sealing member sealing the opening at the distal end of the outer cylinder, and medicine accommodated inside a medicine accommodation part formed inside the outer cylinder; a plunger mountable on the gasket and dismountable from the gasket; the gasket comprising a tubular gasket body and a plunger-mounting member mounted on the gasket body, the tubular gasket body possessing a closed distal end, an open proximal end at which is located an opening, and a lumen part extending from the opening at the proximal end of the tubular gasket body toward the closed distal end; the plunger-mounting member comprising: a tubular body part possessing a hollow part penetrating through the tubular body part from one end of the tubular body part to an opposite end of the tubular body part, the tubular body part also possessing a distal side flange part having a distal end configured to press a proximal end surface of the gasket body; a distal part projecting distally from the tubular body part and configured to be accommodated inside the lumen part of the gasket body, the distal part possessing an outer surface; a spiral rib on the outer surface of the distal part of the plunger-mounting member; a proximal side flange part at a proximal end of the tubular body part; and a plunger-mounting part inside a proximal portion of the tubular body part and on which the plunger is mountable; the tubular gasket body including a spiral screwing part on an inner surface of the tubular gasket body which surrounds the lumen part, the spiral screwing part being engageable with the spiral rib of the plunger-mounting member, the tubular gasket body also including an accommodation part disposed distally from the spiral screwing part of the lumen part for accommodating a portion of the distal part of the plunger-mounting member at which is located the spiral rib; the plunger including a pressing part configured to press a proximal end surface of the proximal side flange part of the plunger-mounting member when mounting the plunger on the gasket, the plunger also including a mounting distal part projecting distally from the pressing part and configured to enter the plunger-mounting part of the plunger-mounting member; the plunger-mounting part of the plunger-mounting member including a spiral concave portion and an engaging rib located at a position in a vicinity of the spiral concave portion and distal from the spiral concave portion; the mounting distal part of the plunger having a spiral projected portion configured to screw engage the spiral concave portion of the plunger-mounting member, the mounting distal part of the plunger also having an engaging portion disposed in a vicinity of the spiral projected portion and at a distal side of the spiral projected portion which engages the engaging rib of the plunger-mounting member; when the plunger-mounting member is mounted on the gasket body, the spiral rib is received in the accommodation part of the tubular gasket body and a distal end of the plunger-mounting member does not contact an inner surface of the tubular gasket body; and when the plunger is mounted on the gasket, the mounting distal part of the plunger does not contact the inner surface of the tubular gasket body.

DETAILED DESCRIPTION

Figure 1:
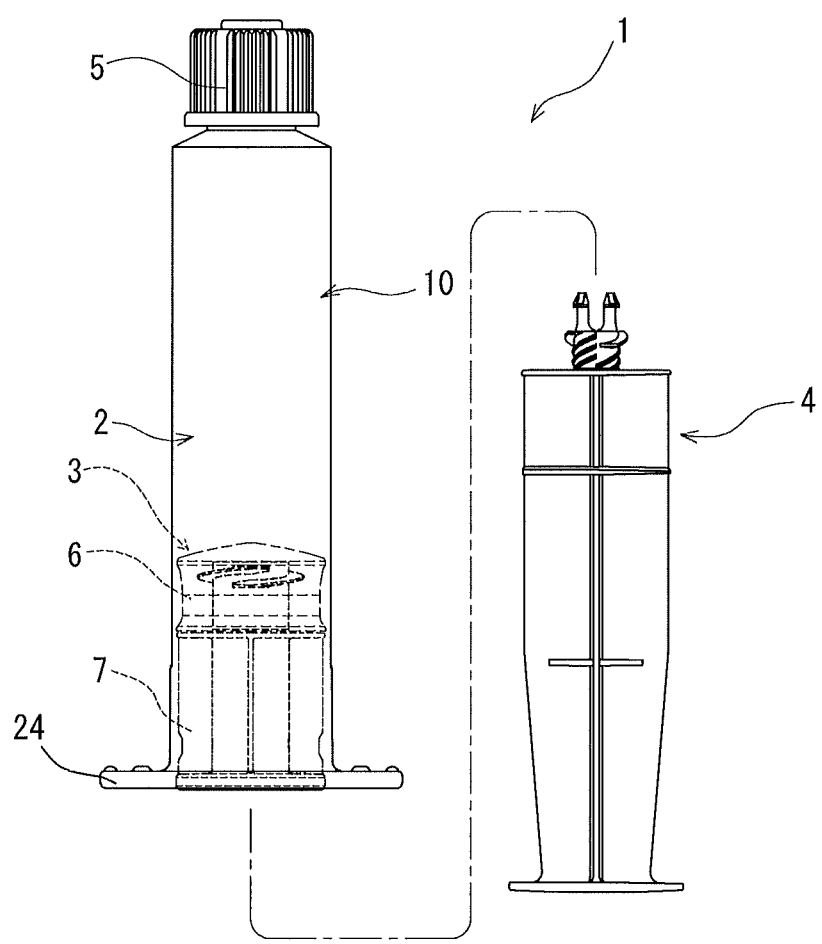
FIG. 1 is a front view of a prefilled syringe of an embodiment of the present invention.

The prefilled syringe of the present invention is described below.

A prefilled syringe 1 of the present invention has a prefilled syringe body 10 including an outer cylinder 2, a gasket 3 slidably accommodated inside the outer cylinder 2, a sealing member 5 for sealing an opening formed at a distal end of the outer cylinder 2, and a medicine 8 accommodated inside a medicine accommodation part formed inside the outer cylinder 2; and a plunger 4 which can be mounted on the gasket 3 and is not mounted thereon.

The gasket 3 is composed of a gasket body 6 which is a tubular body whose distal end is closed and proximal end is open and which has a lumen part 60 extended from an opening formed at the proximal end thereof to a distal side thereof and a plunger-mounting member 7 mounted on the gasket body 6. The plunger-mounting member 7 has a body part 70 which is a tubular body having a hollow part penetrating therethrough from one end thereof to the other end thereof and has a distal side flange part 72 capable of pressing a proximal end surface of the gasket body 6 at a distal side thereof, a distal part 71 which is projected distally from the body'part 70 and can be accommodated inside the lumen part 60 of the gasket body 6, spiral ribs 74, 75 formed on an outer surface of the distal part 71, a proximal side flange part 73 formed at a proximal side of the body part 70, and a plunger-mounting part, formed inside a proximal portion of the body part 70, on which the plunger 4 is to be mounted. The gasket body 6 has a spiral screwing part 63 (63a, 63b), formed on an inner surface of the lumen part 60, which is to screw the spiral ribs 74, 75 of the plunger-mounting member 7 and an accommodation part 62, disposed distally from the spiral screwing part 63 (63a, 63b) of the lumen part 60, for accommodating a portion of the distal part 71 of the plunger-mounting member 7 where the spiral ribs 74, 75 are formed. The plunger 4 has a pressing part 48 capable of pressing a proximal end surface of the proximal side flange part 73 of the plunger-mounting member 7 in mounting the plunger 4 on the gasket 3 (specifically, in mounting the plunger 4 on the plunger-mounting member 7 of the gasket 3) and a mounting distal part 40, projected distally beyond the pressing part 48, which is capable of entering the plunger-mounting part of the plunger-mounting member 7. The plunger-mounting part of the plunger-mounting member 7 has a spiral concave portion 79 and an engaging rib 76 located at a position in the vicinity of the spiral concave portion 79 and distal therefrom. The mounting distal part 40 of the plunger 4 has a spiral projected portion 42 (42a, 42b) capable of screwing the spiral concave portion 79 of the plunger-mounting member 7 and an engaging portion 41, located at a position in the vicinity of the spiral projected portion 42 and distal therefrom, which engages the engaging rib 76 of the plunger-mounting member 7. When the plunger-mounting member 7 is mounted on the gasket body 6, the spiral ribs 74, 75 are received in the accommodation part 62 of the gasket body 6 and a distal end of the plunger-mounting member 7 does not contact an inner surface of the gasket body 6. When the plunger 4 is mounted on the gasket 3, the mounting distal part 40 of the plunger 4 does not contact the inner surface of the gasket body 6.

The prefilled syringe 1 of the present invention is composed of the prefilled syringe body 10 and the plunger 4 which can be mounted on the prefilled syringe body 10 (gasket 3) and is not mounted thereon normally.

The prefilled syringe body 10 has the outer cylinder 2, the sealing member 5 for sealing the opening formed at the distal end of the outer cylinder 2, the gasket 3 slidably accommodated inside the outer cylinder 2, and the medicine 8 accommodated inside the medicine accommodation part formed inside the outer cylinder 2.

The gasket 3 is composed of the gasket body 6 and the plunger-mounting member 7 mounted thereon.

As shown in FIGS. 1 through 6, the gasket body 6 is the tubular body having the closed distal end and the lumen part 60 extended from the opening formed at the proximal end of the gasket body 6 toward the distal side thereof. The gasket body 6 has a tapered part 61 the diameter of which taperingly decreases toward the distal end thereof. The gasket body 6 has a distal side annular rib 68 formed at a distal side of an outer surface thereof and a proximal side annular rib 69 formed at a proximal side of the outer surface thereof.

The gasket body 6 has the lumen part 60 having the function of mounting the plunger-mounting member 7 thereon. The lumen part 60 has on its inner surface the spiral screwing part 63 which is to screw the spiral ribs 74, 75 of the plunger-mounting member 7 and the accommodation part 62, disposed distally from the spiral screwing part 63, for accommodating the portion of the distal part 71 of the plunger-mounting member 7 where the spiral ribs 74, 75 are formed. In this embodiment, the gasket body 6 has an annular projected part 64, for preventing the removal of the plunger-mounting member 7 from the gasket body 6, located at a position in the vicinity of the spiral screwing part 63 and distal therefrom. The annular projected part 64 has a guide portion 65 for guiding the spiral ribs 74, 75 formed on the distal part 71 of the plunger-mounting member 7 to the accommodation part 62, when the spiral ribs 74, 75 reach the annular projected part 64 owing to the progress of screwing between the spiral ribs 74, 75 and the spiral screwing part 63 of the gasket body 6. The guide portion 65 is formed of a rib-absent portion. The guide portion does not necessarily have to be formed of the rib-absent portion, but may be formed of a concave portion, a thin portion or the like. The entire annular projected part 64 may be formed fraily. In this embodiment, the accommodation part 62 is disposed distally from the annular projected part 64.

The spiral screwing part 63 has a start point 63a located at a position in the vicinity of the opening of the lumen part 60, is extended toward the distal side of the gasket body 6 by a predetermined length, and has a termination point 63b located at a position in the vicinity of the rib-absent portion 65 of the annular projected part 64.

Figure 5:
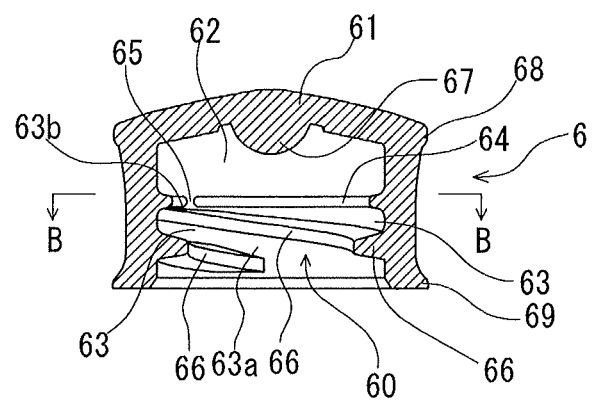
FIG. 5 is a sectional view of a gasket body to be used for the gasket shown in FIG. 3.
Figure 6:
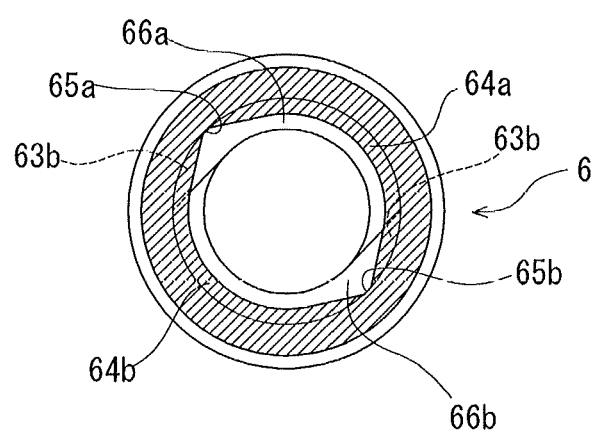
FIG. 6 is a sectional view taken along a line B-B of FIG. 5.
Figure 7:
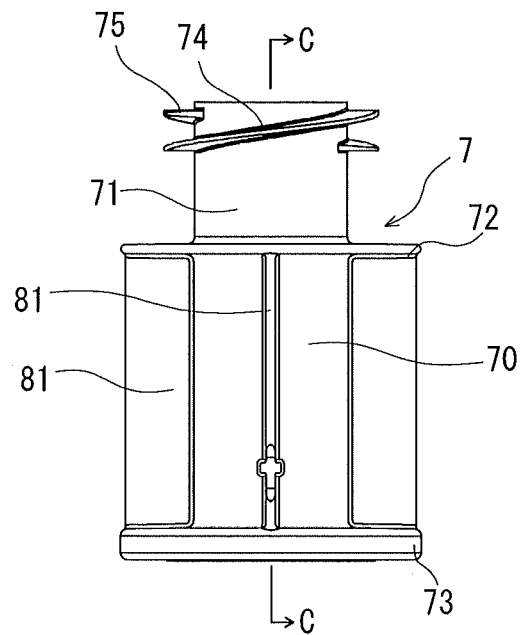
FIG. 7 is a front view of a plunger-mounting member to be used for the gasket shown in FIG. 3.
Figure 8:
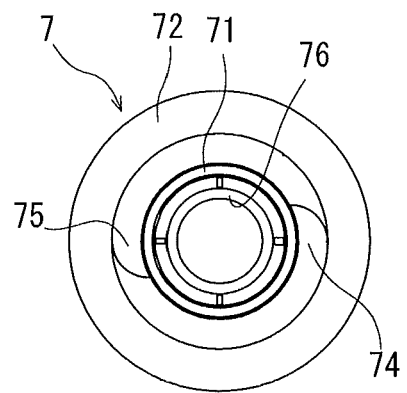
FIG. 8 is a plan view of the plunger-mounting member shown in FIG. 7.

In this embodiment, the spiral screwing part 63 is composed of two lines (two pieces) so that the spiral screwing part 63 corresponds to the spiral ribs 74, 75 formed on the distal part 71 of the plunger-mounting member 7. To form the spiral screwing part 63 of the two lines (two pieces), as shown in FIGS. 5 and 6, the gasket body 6 of this embodiment has two lines of the spiral projections 66a, 66b. Although it is preferable that the gasket body 6 has a plurality (specifically, two lines) of the spiral screwing parts 63, the spiral screwing part (spiral projection) may be composed of only one line (one piece).

In this embodiment, the spiral screwing part 63 is a groove-like part formed between the spiral projections 66 projected from the inner wall surface of the lumen part 60 of the gasket body 6. The spiral screwing part 63 is capable of screwing the spiral ribs 74, 75 of the plunger-mounting member 7 and guiding the spiral ribs 74, 75 toward the distal side of the gasket body 6. The spiral projection 66 has a start point located at a position in the vicinity of the opening of the lumen part 60, is extended toward the distal side of the gasket body 6 by the predetermined length, and has a termination point at a position slightly across the rib-absent portion 65 of the annular projected part 64.

The gasket body 6 has the annular projected part 64, for preventing the removal of the plunger-mounting member 7 from the gasket body 6, formed on the inner surface of a portion located at a position in the vicinity of the spiral screwing part 63 and distal therefrom. In the gasket 3 of this embodiment, the annular projected part 64 is extended almost orthogonally to the axis thereof. Although it is desirable that the annular projected part 64 is extended almost orthogonally to the axis of the gasket 3, the annular projected part 64 may be a little oblique to the orthogonal state.

The gasket body 6 has the accommodation part 62, disposed distally from the annular projected part 64, for accommodating the portion of the distal part 71 of the plunger-mounting member 7 where the spiral ribs 74, 75 are formed.

The annular projected part 64 has the guide portion 65 for guiding the spiral ribs 74, 75 formed on the distal part 71 of the plunger-mounting member 7 to the accommodation part 62, when the spiral ribs 74, 75 reaches the annular projected part 64 owing to the progress of the screwing between the spiral ribs 74, 75 and the spiral screwing part 63 of the gasket body 6. As described above, in the gasket body 6 of this embodiment, two lines of the spiral screwing parts 63 are formed in correspondence to the two lines of the spiral ribs 74, 75. As shown in FIG. 6, the rib-absent portion of the annular projected part 64 is formed at two positions substantially opposed to each other so that the rib-absent portion of the annular projected part 64 corresponds to the spiral screwing part 63 composed of the two lines. In other words, as shown in FIG. 6, the gasket body 6 has two separated annular projected parts 64a, 64b and two rib-absent portions 65a, 65b positioned between the annular projected parts 64a and 64b. As also shown in FIG. 6, it is preferable that a rib of the annular projected part 64 (64a, 64b) becomes gradually smaller toward the rib-absent portion 65 (65a, 65b). The rib may become gradually smaller in its width or height or gradually smaller in its width and height toward the guide portion 65 (65a, 65b).

The above-described construction allows the spiral ribs 74, 75 of the plunger-mounting member 7 to easily pass through the annular projected part 64, in other words, to easily enter the accommodation part 62. The rib of the rib-absent portion does not necessarily have to be completely absent, but may be absent to such an extent that the rib-absent portion has the function of guiding the spiral ribs 74, 75 of the plunger-mounting member 7 to the accommodation part 62.

As shown in FIG. 5, the width of the spiral screwing part 63, in other words, the distance between the spiral projection 66 and the annular projected part 64 becomes narrower toward the rib-absent portion 65 (also toward the termination point 63b of the spiral screwing part 63). Therefore the spiral ribs 74, 75 of the plunger-mounting member 7 can be securely guided to the rib-absent portion 65 of the annular projected part 64. It is preferable that the projected height of the spiral projection 66 for forming the spiral screwing part 63 of the gasket body 6 is higher than that of the annular projected part 64.

Although the height of the annular projected part 64 is different according to the size of the gasket body 6, the height thereof is favorably 1.0 to 3.0 mm and especially favorably 1.5 to 2.5 mm. The width of the rib-absent portion 65 of the annular projected part 64 (the width of the rib-absent portion 65 in the circumferential direction of the gasket) is favorably 0.5 to 3.0 mm and especially favorably 0.5 to 1.5 mm.

The gasket body 6 has a convex portion 67 projected from a central portion of the inner surface of the distal portion thereof toward the proximal side thereof. The convex portion 67 may be so constructed that it contacts the distal end 79 of the distal part 71 of the plunger-mounting member 7, when the distal portion of the gasket body 6 deforms toward its proximal side. It is preferable that the convex portion 67 is approximately semispherical. Generally the diameter of the gasket body 6 is 5 to 30 mm, and the whole length thereof is 5 to 30 mm.

As constituent materials of the gasket body 6, known materials conventionally used for the gasket can be used. For example, rubber, elastomer, polyolefin resin, fluororesin, and polyester resin are listed. As the rubber, natural rubber, isoprene rubber, butyl rubber, chloroprene rubber, nitrile-butadiene rubber, styrene-butadiene rubber, and silicone rubber are favorable. It is especially favorable to vulcanize the above-described rubbers. As the elastomer, polyvinyl chloride elastomer, polyolefin elastomer, styrene elastomer, polyester elastomer, polyamide elastomer, polyurethane elastomer, and mixtures of these elastomers are favorable. Of the above-described rubbers and elastomers, the styrene-butadiene rubber, the butyl rubber, and the styrene elastomer are preferable because these materials have suitable hardnesses and elastic properties and various sterilization methods such as $\gamma$ ray sterilization, electron beam sterilization, and high-pressure steam sterilization can be adopted therefor.

The front side of the gasket body 6 may be coated with a low medicine absorbable substance or the like.

As materials of a low medicine absorbable layer, known materials which are conventionally used for a laminate gasket can be used. As the materials of the low medicine absorbable layer, polyolefin resin, fluororesin, and polyester resin are listed. Specifically, as the polyolefin resin, polypropylene, ultra-high-molecular-weight polyethylene, poly (4-methyl-pentene-1), and cyclic polyolefin are preferable. As the fluororesin, a tetrafluoroethylene-perfluoroethoxyethylene copolymer, polytetrafluoroethylene, a tetrafluoroethylene/perfluoroalkyl vinyl ether copolymer, a tetrafluoroethylene/hexafluoropropylene copolymer are preferable.

It is preferable to apply a lubricant to the outer surface of the gasket body 6 and to at least the surface of each of the distal side annular rib 68 and the proximal side annular rib 69. The lubricant may be applied to the inner surface of the outer cylinder. As the lubricant, silicone oil is suitable. By forming a silicone resin layer formed by solidifying the silicone resin on the surface of the gasket body, it is possible to eliminate the need for the use of the lubricant such as the silicone oil.

As shown in FIGS. 2 through 11, the plunger-mounting member 7 is a tubular body, having a predetermined length, which has a hollow part penetrating therethrough from one end thereof to the other end thereof.

The plunger-mounting member 7 has the body part 70, the distal part 71 which is projected distally from the body part 70 and can be accommodated inside the lumen part 60 of the gasket body 6, and the plunger-mounting part, formed inside the proximal portion of the body part 70, on which the plunger 4 is to be mounted.

The body part 70 is the tubular body which has a predetermined length and the plunger-mounting part at its proximal portion. At a plunger-mounting time, the plunger-mounting part of the plunger-mounting member 7 is visible. Therefore watching the plunger being mounted on the plunger-mounting part, it is possible to mount the plunger on the plunger-mounting part and thus perform the plunger-mounting work at ease and securely.

The tubular body part 70 having the predetermined length has a plurality of side plate portions 81 axially extended on its side surface. The body part 70 has the disk-shaped distal side flange part 72 capable of pressing the proximal end surface of the gasket body 6 at the distal end thereof. The body part 70 has the disk-shaped proximal side flange part 73 capable of contacting the pressing part 48 of the plunger 4 at the proximal end thereof. A plurality of the side plate portions 81 connects the distal side flange part 72 and the proximal side flange part 73 to each other and reinforces both flange parts 72 and 73.

Figure 9:
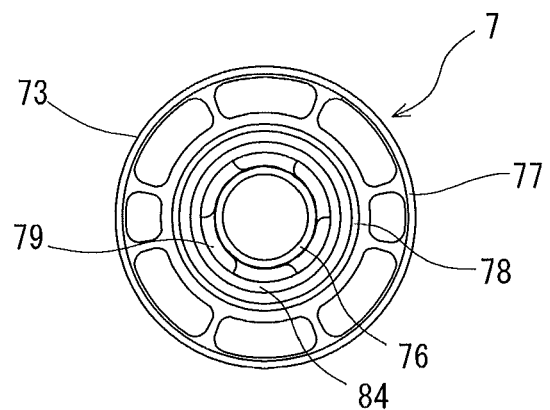
FIG. 9 is a bottom view of the plunger-mounting member shown in FIG. 7.
Figure 10:
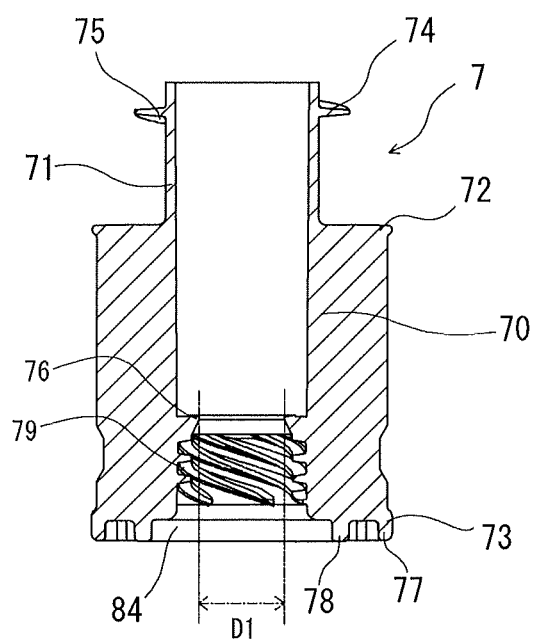
FIG. 10 is a sectional view taken along a line C-C of FIG. 7.
Figure 11:
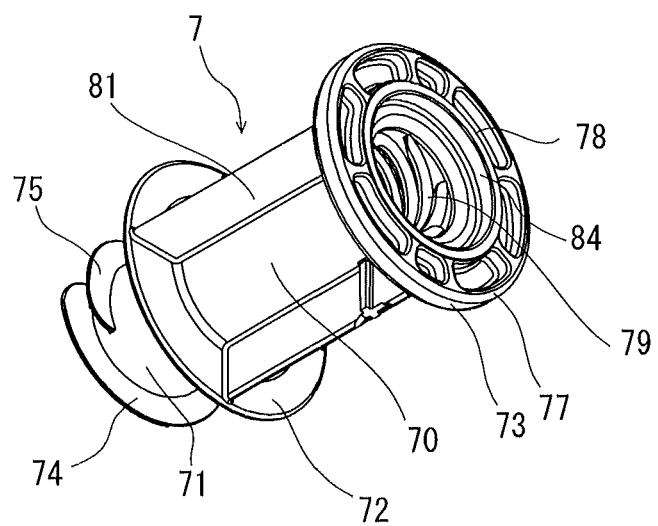
FIG. 11 is a perspective view as viewed from a bottom surface side of the plunger-mounting member shown in FIG. 7.

The outer edge of the distal side flange part 72 is almost circular. The outer diameter of the distal side flange part 72 is set a little smaller than that of the proximal end of the gasket body 6. The peripheral portion of the distal side flange part 72 at its distal end is formed as a flat surface and contacts and is capable of pressing the proximal end surface of the gasket body 6. In this embodiment, as shown in FIGS. 9 through 11, the proximal side flange part 73 has a flat plate portion and a collar portion having a predetermined length extended from the flat plate portion toward the proximal end of the plunger-mounting member 7. In the plunger-mounting member 7 of this embodiment, the proximal side flange part 73 has an outer collar 77 and an inner collar 78 both extended a little from the flat plate portion toward the proximal end of the plunger-mounting member 7. The outer collar 77 and the inner collar 78 are concentrically formed. The distal end (free end) of the outer collar 77 and that of the inner collar 78 are flatly formed. The distal end (free end) of the inner collar 78 is projected by a small amount beyond the distal end (free end) of the outer collar 77.

The distal part 71 projected from the body part 70 is a cylindrical part which has an almost equal outer diameter and a predetermined length. The distal part 71 is formed shorter than the body part 70. The distal part 71 is projected distally from the vicinity of the center of the distal side flange part 72 of the body part 70. In a normal state of the gasket body 6, namely, in a state in which the gasket body 6 does not deform, the distal part 71 does not contact the inner surface of the distal portion of the gasket body 6.

The spiral ribs 74, 75 are formed on the outer surface of the distal portion of the distal part 71 of the plunger-mounting member 7. As shown in FIGS. 4, 7, 8, 10, and 11, in the plunger-mounting member 7 of this embodiment, in correspondence to the spiral screwing part 63 of the gasket body 6, two lines of the spiral ribs 74, 75 are formed. Each of the spiral ribs 74, 75 has a start point located at a position in the vicinity of the distal end of the distal part 71 of the plunger-mounting member 7 and is extended toward the proximal side of the distal part 71 by a predetermined length. Although it is preferable that the plunger-mounting member 7 has a plurality of the spiral ribs (specifically, two lines), the spiral rib may be composed of only one line (one piece).

It is preferable that the height of the annular projected part 64 of the gasket body 6 and that of the spiral rib of the plunger-mounting member 7 are set as described below: The height of the annular projected part 64 of the gasket body is favorably 1.0 to 3.0 mm and more favorably 1.5 to 2.5 mm. The height of the spiral rib of the plunger-mounting member 7 is favorably 2.5 to 3.2 mm, more favorably 2.8 to 3.1 mm, and most favorably 2.95 to 3.05 mm. The width of a contact portion of the annular projected part and the spiral rib are favorably 0.5 to 2.5 mm and especially favorably 1.0 to 2.3 mm. The inner diameter of the annular projected part 64 of the gasket body 6 is favorably 16.0 to 20.0 mm and especially favorably 17.0 to 19.0 mm. The outer diameter of the spiral rib of the plunger-mounting member 7 is favorably 19.0 to 22.0 mm and especially favorably 20.0 to 21.0 mm.

The plunger-mounting part for accommodating the mounting distal part 40 of the plunger 4 to be described later therein and mounting the mounting distal part 40 thereon is formed on the inner surface of the hollow part of plunger-mounting member 7. The plunger-mounting part has the spiral concave portion 79 on which the spiral projected portion 42 (42a, 42b) of the mounting distal part 40 is to screw and the engaging rib 76, located at a position in the vicinity of the spiral concave portion 79 and distal therefrom, which is to engage the engaging portion 41 of the mounting distal part 40. As shown in FIGS. 9 through 11, the plunger-mounting member 7 has a large-diameter opening 84 at its proximal end. The spiral concave portion 79 is formed on the inner surface of a lumen part having a smaller diameter than the large-diameter opening 84. The spiral concave portion 79 has a start point at a position a little distal from the opening formed at the proximal end of the plunger-mounting member 7 and is extended toward the distal side of the plunger-mounting member 7 by a predetermined length. The plunger-mounting part has two lines (two pieces) of the spiral concave portion 79. Although it is preferable that the plunger-mounting part has a plurality of (specifically, two lines) the spiral concave portions, the spiral concave portion may be composed of only one line (one piece).

The plunger-mounting part has the engaging rib 76 located at a position in the vicinity of the spiral concave portion 79 and distal therefrom. The engaging rib 76 engages the engaging portion 41 of the mounting distal part 40 of the plunger 4 to be described later. The inner surface of the engaging rib 76 forms an annular tapered configuration which tapers such that the diameter of the engaging rib 76 becomes gradually smaller toward the distal end thereof. This construction allows the engaging portion 41 of the plunger 4 to be described later to easily approach the engaging rib 76 and pass therethrough. The distal end surface of the engaging rib 76 is formed erectly from the body part 70, in other words, as an annular flat surface almost orthogonal to the axis of the body part 70. Therefore the engaging rib 76 which has engaged the engaging portion 41 of the plunger 4 to be described later is prevented from separating therefrom. Although it is preferable that the engaging rib 76 is annular, the engaging rib 76 may be dashed line-shaped (uncontinuous).

As the material for forming the plunger-mounting member 7, it is preferable to use hard or semi-hard resin such as high-density polyethylene, polypropylene, polystyrene, and polyethylene terephthalate.

Figure 2:
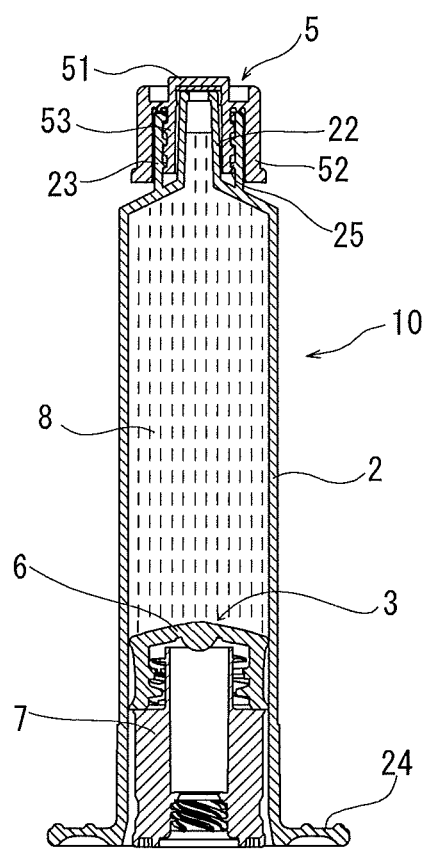
FIG. 2 is a vertical sectional view of a prefilled syringe body of the prefilled syringe shown in FIG. 1.
Figure 3:
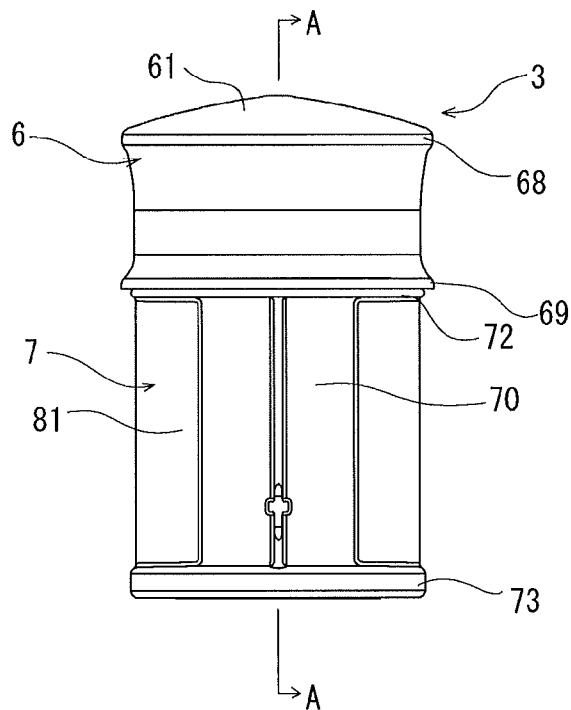
FIG. 3 is an enlarged front view of a gasket to be used for the prefilled syringe of the present invention.

As shown in FIGS. 1 through 4, in the prefilled syringe of the present invention, the outer cylinder 2 accommodates the gasket 3 having the gasket body 6 on which the plunger-mounting member 7 has been mounted. As shown in FIGS. 1 and 2, it is preferable that the proximal end of the plunger-mounting member 7 is not substantially projected beyond the proximal end of the outer cylinder 2. The plunger-mounting member 7 is mounted on the gasket body 6, as described below.

Figure 4:
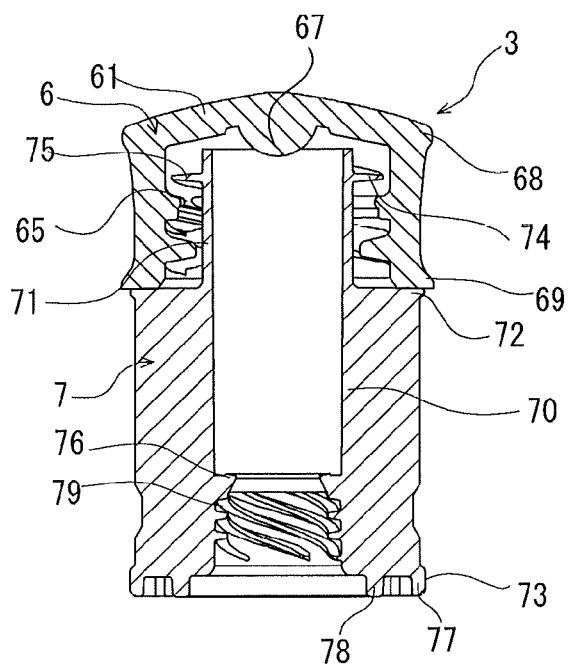
FIG. 4 is a sectional view taken along a line A-A of FIG. 3.

After the spiral ribs 74, 75 of the plunger-mounting member 7 are inserted into the gasket body 6 from the start point of the spiral screwing part 63, the plunger-mounting member 7 is rotated. Thereby the screwing between the spiral ribs 74, 75 and the spiral screwing part 63 progresses. During the progress of the screwing therebetween, the start points of the spiral ribs 74, 75 of the plunger-mounting member 7 approach the termination point of the spiral screwing part 63 of the gasket body 6 and the rib-absent portion 65 of the annular projected part 64 of the gasket body 6 and are positioned between the spiral projection 66 forming the spiral screwing part 63 of the gasket body 6 and the annular projected part 64 thereof. By further rotating the plunger-mounting member 7, the spiral ribs 74, 75 pass the rib-absent portion 65 of the annular projected part 64 and enter the accommodation part 62. By continuing to rotate the plunger-mounting member 7, as shown in FIG. 4, the spiral ribs 74, 75 entirely pass the rib-absent portion 65 of the annular projected part 64, and the portion of the distal part 71 of the plunger-mounting member 7 where the spiral ribs are formed is accommodated inside the accommodation part 62 of the gasket body 6. Thereby the work of mounting the plunger-mounting member 7 on the gasket body 6 finishes. In the state in which the plunger-mounting member 7 is mounted on the gasket body 6, the proximal end surfaces of the spiral ribs 74, 75 of the plunger-mounting member 7 contact the distal end surface of the annular projected part 64 of the gasket body 6. Therefore the plunger-mounting member 7 is prevented from separating from the gasket body 6. In the state in which the portion of the distal part 71 of the plunger-mounting member 7 where the spiral ribs are formed is accommodated inside the accommodation part 62 of the gasket body 6, the plunger-mounting member 7 runs idle. When the plunger-mounting member 7 rotates in either direction in a normal state, the proximal ends of the spiral ribs 74, 75 do not enter the rib-absent portion 65 of the annular projected part 64. Therefore the separation of the plunger-mounting member 7 from the gasket body 6 and the rotation of the gasket body 6 are restrained, when the plunger-mounting member 7 rotates. The plunger-mounting member 7 is mounted on the gasket body 6 with the spiral ribs 74, 75 of the plunger-mounting member 7 being accommodated inside the accommodation part 62 of the gasket body 6 such that the distal end of the plunger-mounting member 7 does not contact the inner surface of the gasket body 6.

As shown in FIGS. 1, 12 through 15, the plunger 4 has the pressing part 48 capable of pressing the proximal end surface of the proximal side flange part 73 of the plunger-mounting member 7 in mounting the plunger 4 on the gasket 3 (specifically, in mounting the plunger 4 on the plunger-mounting member 7 of the gasket 3) and the mounting distal part 40, projected distally from the pressing part 48, which is capable of entering the plunger-mounting part of the plunger-mounting member 7. When the plunger 4 is mounted on the gasket 3, the distal portion 42 of the plunger 4 does not contact the inner surface of the gasket body 6.

Figure 12:
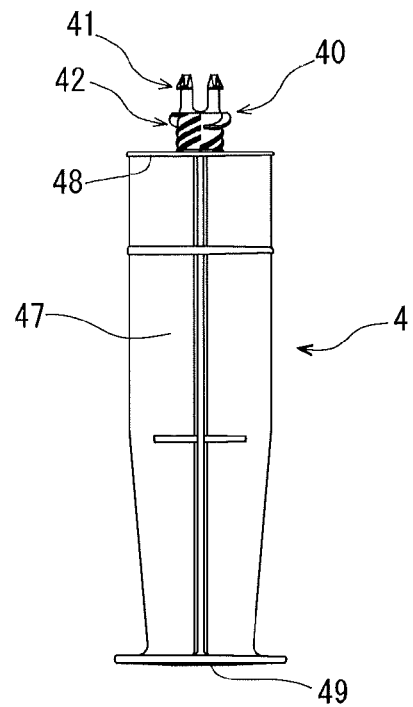
FIG. 12 is an enlarged front view of a plunger to be used for the prefilled syringe of the present invention.
Figure 13:
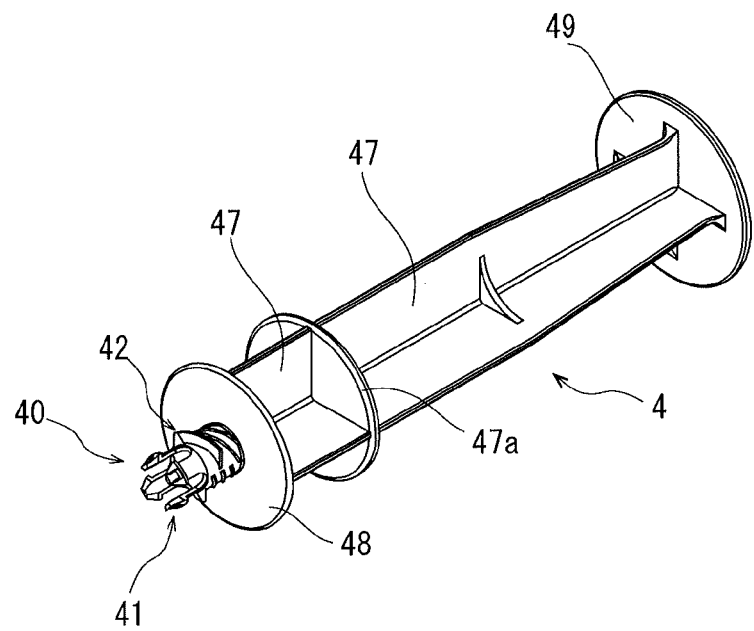
FIG. 13 is a perspective view of the plunger shown in FIG. 12.
Figure 14:
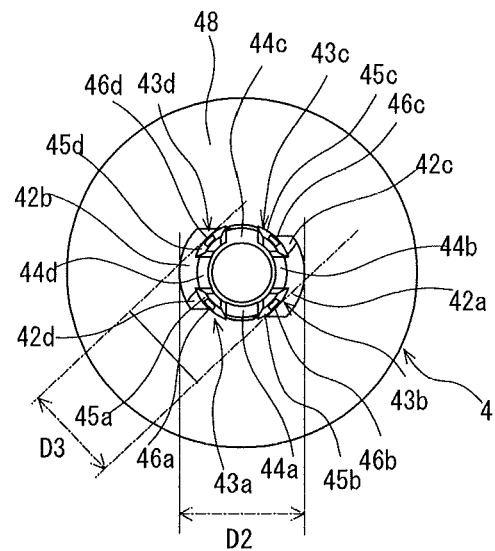
FIG. 14 is an enlarged plan view of the plunger shown in FIG. 12.
Figure 15:
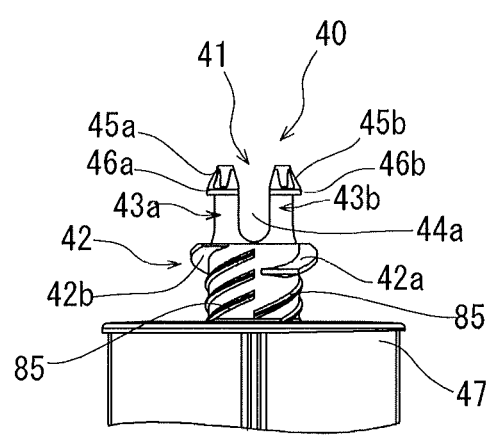
FIG. 15 is an enlarged front view of a front side of the plunger shown in FIG. 12.

As shown in FIGS. 12 and 13, the plunger 4 has a shaft part 47 formed sectionally crosswise. The pressing part 48 is formed at the distal end of the shaft part 47. The pressing part 48 is formed in the shape of a disk so that it is capable of pressing the proximal end surface of the plunger-mounting member 7. A reinforcing rib 47a is formed midway on the shaft part 47. A plunger-pressing part 49 is formed at the proximal end of the shaft part 47.

The mounting distal part 40 of the plunger 4 is a small-diameter tubular part which is projected distally from the pressing part 48 and has the spiral projected portion 42 (42a, 42b) capable of screwing the spiral concave portion 79 of the plunger-mounting member 7 and the engaging portion 41, located at a position in the vicinity of the spiral projected portion 42 and distal therefrom, which engages the engaging rib 76 of the plunger-mounting member 7.

The engaging portion 41 is formed at the distal end of the plunger 4. As shown in FIGS. 12 through 15 and 21, the engaging portion 41 of the plunger 4 of this embodiment is constructed of convex portions 46a, 46b, 46c, and 46d formed on the outer surfaces of claw portions 43a, 43b, 43c, and 43d of the plunger 4. The convex portions 46a, 46b, 46c, and 46d are projected portions formed proximally from the distal ends of the claw portions 43a, 43b, 43c, and 43d by a predetermined length. By pressing the distal portion 42 of the plunger 4 into the hollow part of the plunger-mounting member 7, the convex portions 46a, 46b, 46c, and 46d ride across and engage the engaging rib 76 of the plunger-mounting member 7.

As shown in FIGS. 12 through 15, in the plunger 4 of this embodiment, a plurality of the claw portions 43a, 43b, 43c, and 43d is disposed on substantially the same circumference. Specifically, a plurality (specifically, four) of the claw portions 43a, 43b, 43c, and 43d is so disposed that the adjacent claw portions form equal angles with the axis of the plunger 4. Slits 44a, 44b, 44c, and 44d are formed between the adjacent claw portions. The slits 44a, 44b, 44c, and 44d are disposed proximally from the distal end of the distal portion 42 and extended beyond the portion where the convex portions 46a, 46b, 46c, and 46d are formed. The outer surfaces of the claw portions 43a, 43b, 43c, and 43d are formed as inclined surfaces 45a, 45b, 45c, and 45d which incline from the distal ends of the claw portions to the convex portions. The above-described construction facilitates the engagement between the engaging portion 41 and the engaging rib 76 of the plunger-mounting member 7. The claw portions 43a, 43b, 43c, and 43d elastically deform inward to a small extent in mounting the plunger 4 on the plunger-mounting member 7. The proximal end surfaces of the convex portions 46a, 46b, 46c, and 46d are formed erectly from the claw portions 43a, 43b, 43c, and 43d, in other words, as annular flat surfaces almost orthogonal to the axis of the plunger 4. Therefore the engaging rib 76 which has engaged the engaging portion 41 of the plunger 4 to be described later is prevented from separating therefrom. The number of the claw portions is not limited to four, but is preferably three to eight.

Figure 16:
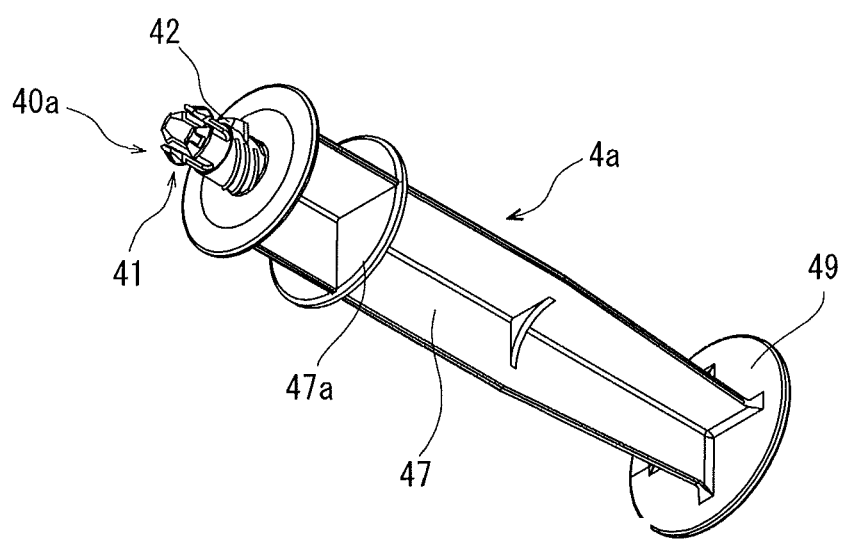
FIG. 16 is a perspective view of a plunger of another example to be used for the prefilled syringe of the present invention.

The spiral projected portion 42 is formed in proximity to the engaging portion 41 and at the proximal side thereof. As shown in FIGS. 12 through 15 and 21, in the plunger 4 of this embodiment, the spiral projected portion 42 (42a, 42b) is formed on the outer surface of the central portion of the tubular part in which the mounting distal part 40 is formed. As shown in FIGS. 12 through 15, in the plunger 4 of this embodiment, two lines (two pieces) of the spiral projected portions 42a, 42b are formed in correspondence to the spiral concave portion 79 of the plunger-mounting member 7. Each of the spiral projected portions 42a, 42b is short and has a start point and a termination point at the central portion of the tubular part in which the mounting distal part 40 of the plunger 4 is formed. Although it is preferable that the plunger 4 has a plurality (specifically, two lines) of the spiral projected portions, the spiral projected portion may have only one line (one piece) of rib like a mounting distal part 40a of a plunger 4a shown in FIG. 16.

It is preferable that the depth of an annular concave part of the plunger-mounting member 7 and the height of the spiral projected portion of the plunger 4 are set as described below: The depth of the annular concave part of the plunger-mounting member 7 is favorably 1.0 to 3.0 mm and especially favorably 1.5 to 2.5 mm. The height of the spiral projected portion of the plunger 4 is favorably 2.5 to 3.2 mm, more favorably 2.8 to 3.1 mm, and most favorably 2.95 to 3.05 mm. The width of a contact portion of the annular concave part and a contact portion of the spiral projected portion is favorably 0.5 to 2.5 mm and especially favorably 1.0 to 2.3 mm. The inner diameter (D1 in FIG. 10) of the engaging rib 76 of the plunger-mounting member 7 is favorably 7 to 9 mm and especially favorably 7.5 to 8.5 mm. The outer diameter (D2 in FIG. 14) of the spiral projected portion of the plunger 4 is favorably 10.0 to 14.0 mm and especially favorably 10 to 13 mm. The outer diameter (D3 in FIG. 14) of the engaging portion 41 which engages the engaging rib 76 of the plunger-mounting member 7 is favorably 7.5 to 10.5 mm and especially favorably 9 to 10 mm.

Figure 21:
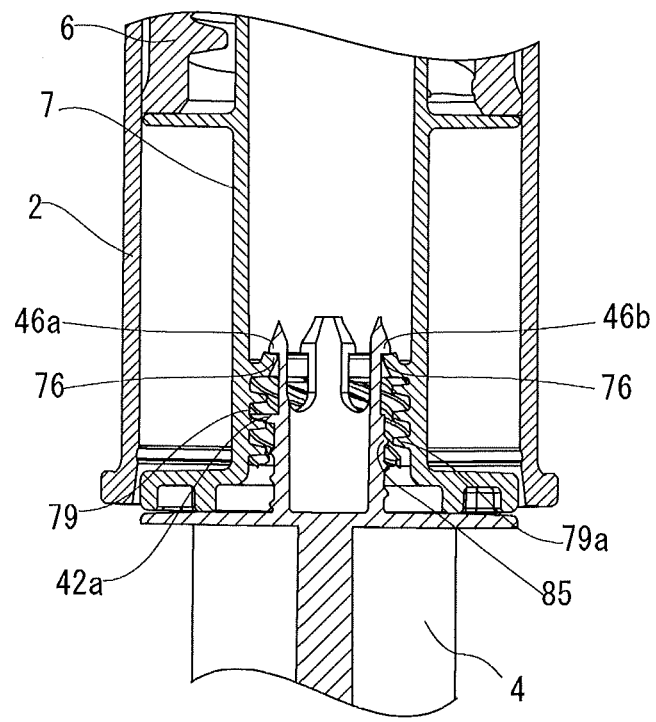
FIG. 21 is an explanatory view for explaining the action in mounting the plunger on the prefilled syringe body of the prefilled syringe of the present invention.

Flat portions 42c, 42d (plane portion, orthogonal to the axis of the tubular part, which forms the mounting distal part 40) are formed at distal ends of the spiral projected portions 42a, 42b respectively. The spiral projected portions 42a, 42b are spirally extended from the proximal ends of the flat portions 42c, 42d respectively toward the proximal side of the mounting distal part 40. The mounting distal part 40 of the plunger 4 may have a spiral rib 85 the height of which is smaller than that of the spiral projected portion 42 on the outer surface thereof located proximally from the spiral projected portion 42 (42a, 42b). As shown in FIG. 21, the spiral rib 85 is so formed as to confront a spiral mountain portion 79a forming the spiral concave portion 79 of the plunger-mounting member 7, when the plunger 4 is mounted on the plunger-mounting member 7. Therefore when the plunger 4 is mounted on the plunger-mounting member 7, it is possible to decrease a clearance therebetween and prevent the plunger 4 from becoming shaky.

As the material for forming the plunger 4, it is preferable to use hard or semi-hard resin such as high-density polyethylene, polypropylene, polystyrene, and polyethylene terephthalate.

The outer cylinder 2 is a tubular body formed of transparent or semitransparent materials and preferably of materials having low oxygen and vapor permeabilities.

Figure 17:
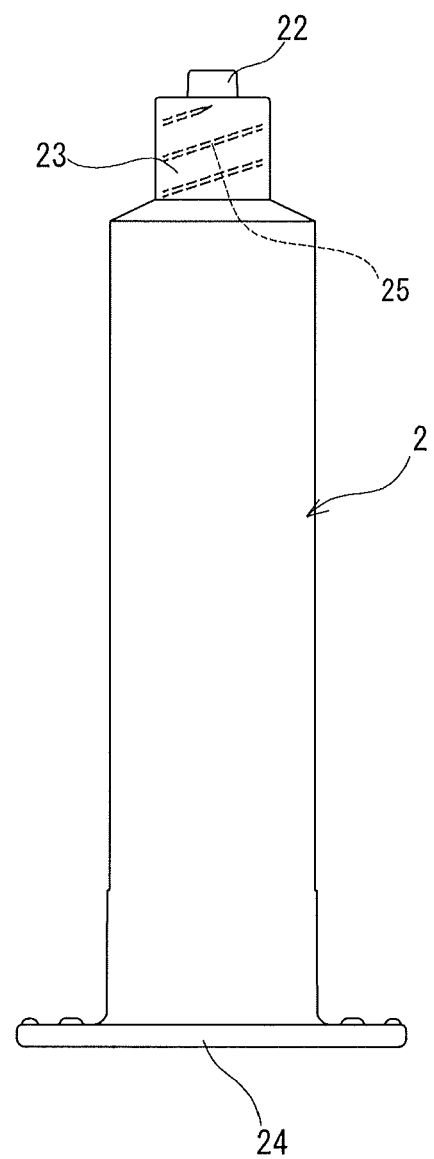
FIG. 17 is a front view of an outer cylinder to be used for the prefilled syringe of the present invention.

As shown in FIGS. 1, 2, and 17, the outer cylinder 2 has a nozzle part 22 and a collar 23.

The nozzle part 22 is formed at the distal end of the outer cylinder 2 and has a distal-end opening for exhausting the medicine and the like filled inside the outer cylinder 2 in such a way that the diameter of the nozzle part 22 taperingly decreases toward the distal end thereof. The collar 23 is formed cylindrically and concentrically with the nozzle part 22 in such a way that the collar 23 surrounds the nozzle part 22. The collar 23 is open at its distal end and almost equal in its inner and outer diameters from its proximal end to distal end. The distal portion of the nozzle part 22 is projected from the opening formed at the distal end of the collar 23. The distal portion of the nozzle part 22 and that of the collar 23 are chamfered to easily accommodate the nozzle part 22 and the collar 23 inside the sealing member (sealing cap) 5.

A thread groove (outer cylinder-side screwing portion) 25 which is to screw a screw thread (cap-side screwing portion) 54 formed on a nozzle accommodation portion 53 of the sealing member (sealing cap) 5 to be described later is formed on the inner circumferential surface of the collar 23. Thereby the outer cylinder 2 and the sealing cap 5 screw each other between the inner circumferential surface of the collar 23 and the outer circumferential surface of the nozzle accommodation portion 53. The thread groove (outer cylinder-side screwing portion) 25 is a portion where a syringe needle (hub of syringe needle) is mounted after the sealing cap 5 is removed from the outer cylinder 2.

As shown in FIGS. 1, 2, and 17, the outer cylinder 2 has a flange 24. The flange 24 is an elliptic donut-shaped disk portion projected from the entire circumference of the proximal end of the outer cylinder 2 at a right angle therewith. As shown in FIGS. 1, 2, and 17, the flange 24 has two wide gripping portions opposed to each other. A plurality of ribs is formed on the surface of each gripping portion at the distal side thereof.

As the material for forming the outer cylinder 2, various resins including polypropylene, polyethylene, polystyrene, polyamide, polycarbonate, polyvinyl chloride, poly-(4-methylpentene-1), acryl resin, an acrylonitrile-butadiene-styrene copolymer, polyester such as polyethylene terephthalate; and cyclic polyolefin are listed. Of these resins, the resins such as the polypropylene and the cyclic polyolefin are preferable because these resins can be easily molded and are heat-resistant.

Figure 18:
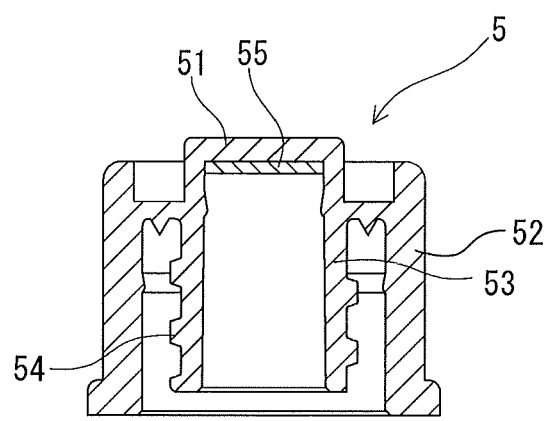
FIG. 18 is a sectional view of a sealing member (sealing cap) to be used for the prefilled syringe of the present invention.

As shown in FIGS. 1, 2, and 18, the sealing cap 5 which is the sealing member has a closed end 51, the nozzle accommodation portion 53, and a collar accommodation portion 52.

The nozzle accommodation portion 53 is disposed at the central portion of the sealing cap 5 and closed at its distal end and cylindrical. The inner diameter of the nozzle accommodation portion 53 is set a little larger than that of the nozzle part 22 and taperingly increases a little from its distal end toward its proximal end so that the nozzle accommodation portion 53 accommodates the entire nozzle part 52 inserted thereinto from an opening formed at its proximal end.

A sealing member 55 for liquid-tightly sealing the opening formed at the distal end of the outer cylinder 2 is accommodated on an inner closed surface (inner surface of closed end 51) of the nozzle accommodation portion 53. It is preferable that the sealing member 55 is elastic so that the sealing member 55 is capable of liquid-tightly sealing the opening formed at the distal end of the outer cylinder 2. As the material for forming the sealing member 55, it is preferable to use natural rubber; synthetic rubber such as isoprene rubber, butadiene rubber, fluororubber, and silicone rubber; and thermoplastic elastomer such as olefin elastomer and styrene elastomer.

The screw thread (cap-side screwing portion) 54 to screw the thread groove (outer cylinder-side screwing portion) 25 formed on the inner surface of the collar 23 of the outer cylinder 2 is formed on the outer surface of the nozzle accommodation portion 53. Thereby the outer cylinder 2 and the sealing cap 5 screw each other between the outer surface of the nozzle accommodation portion 53 and the inner surface of the collar 23.

The collar accommodation portion 52 is a cylindrical body so formed that it surrounds the nozzle accommodation portion 53 and is closed at its distal end. The collar accommodation portion 52 accommodates the collar 23 between the inner surface of the collar accommodation portion 52 and the outer surface of the nozzle accommodation portion 53. The cylindrically formed collar accommodation portion 52 is concentric with the nozzle accommodation portion 53. The inner diameter of the collar accommodation portion 52 is almost equal from its distal end to proximal end.

As shown in FIG. 1, the outer side surface (outer circumferential surface of the collar accommodation portion 52) of the sealing cap 5 is vertically notched to prevent fingers from slipping in rotating the sealing cap 5.

As the material for forming the sealing cap, various resins including polypropylene, polyethylene, polystyrene, polyamide, polycarbonate, polyvinyl chloride, poly-(4-methylpentene-1), acryl resin, the acrylonitrile-butadiene-styrene copolymer, polyester such as polyethylene terephthalate; and cyclic polyolefin are listed. Of these resins, the resins such as the polypropylene and the cyclic polyolefin are preferable because these resins can be easily molded and are heat-resistant.

In the prefilled syringe 1 of the present invention, as shown in FIG. 2, the medicine 8 is filled inside the medicine accommodation part formed inside the outer cylinder 2.

As the medicine 8, any medicines can be used. For example, a medicinal solution such as ciclosporin, benzodiazepine medicines, a sodium chloride injection solution, vitamin preparations, and minerals; and powdery, frozen dry medicine or liquid medicine such as antibacterial agents, protein formulations, and the like are used. The prefilled syringe of the present invention is suitable for a prefilled syringe of a type which administers a medicine to a patient by using a syringe pump. Thus as medicines to be filled in the prefilled syringe, those suitable for the use of administering means using the syringe pump are preferable. Thus a nitroglycerin injection solution, an isosorbide dinitrate injection solution, a dopamine hydrochloride injection solution, a dobutamine hydrochloride injection solution, and a morphine hydrochloride injection solution are listed.

Figure 19:
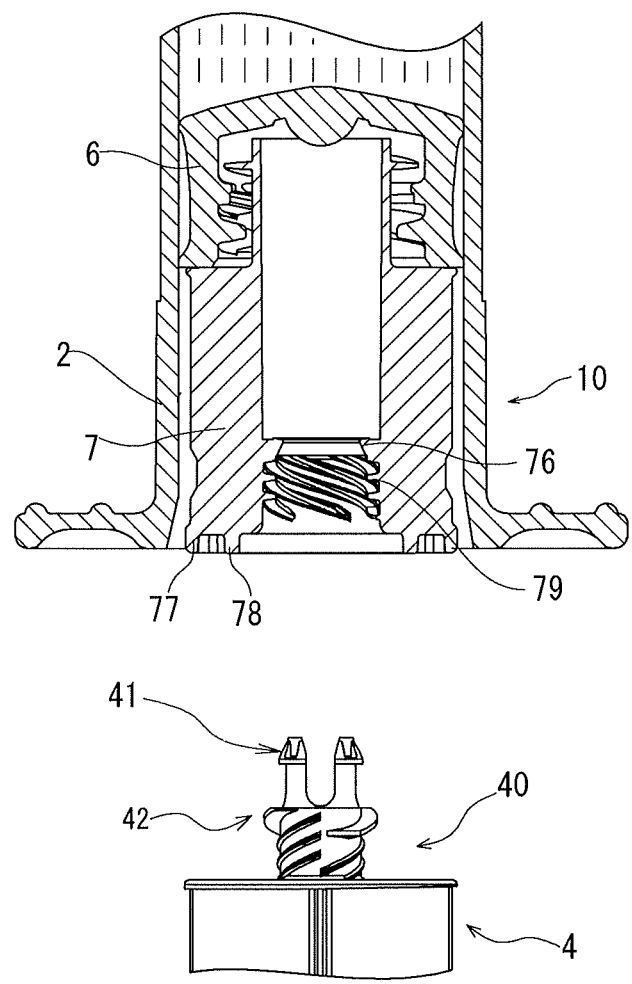
FIG. 19 is an explanatory view for explaining the action in mounting the plunger on a prefilled syringe body of the prefilled syringe of the present invention.
Figure 20:
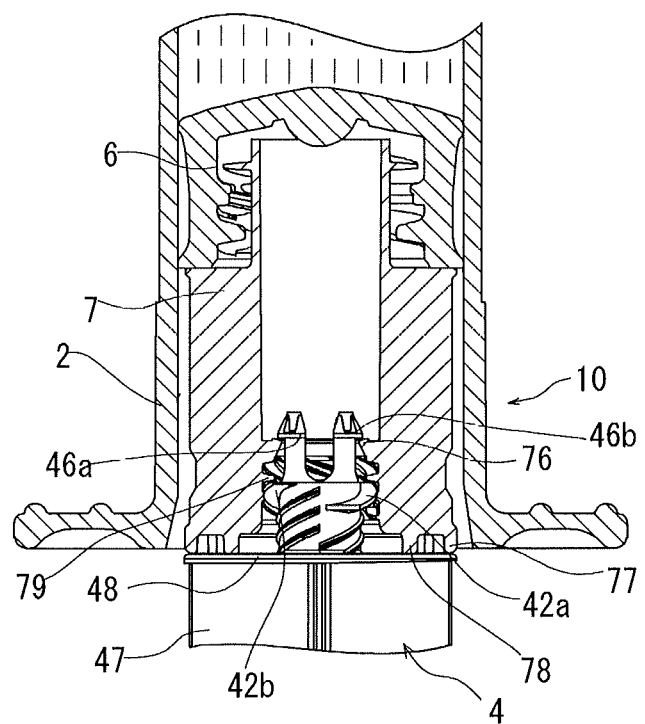
FIG. 20 is an explanatory view for explaining the action in mounting the plunger on the prefilled syringe body of the prefilled syringe of the present invention.

The action of the prefilled syringe 1 of the present invention is described below with reference to FIGS. 19 through 21.

In the prefilled syringe body 10, the gasket 3 is accommodated inside the proximal portion of the outer cylinder 2. As shown in FIG. 19, the plunger 4 is entered into the hollow part of the plunger-mounting member 7 from the mounting distal part 40 of the plunger 4 with the plunger 4 being rotated. Thereby the spiral projected portion 42 (42a, 42b) of the mounting distal part 40 of the plunger 4 screws the spiral concave portion 79 of the plunger-mounting part of the plunger-mounting member 7. During the progress of the screwing therebetween, the engaging portion 41 of the mounting distal part 40 of the plunger 4 proceeds toward the engaging rib 76 of the plunger-mounting member 7. As a result, the convex portions 46a, 46b, 46c, and 46d of the claw portions 43a, 43b, 43c, and 43d of the plunger 4 ride across the engaging rib 76 of the plunger-mounting member 7. As shown in FIGS. 20 and 21, the convex portions 46a, 46b, 46c, and 46d engage the engaging rib 76 of the plunger-mounting member 7. In this manner, the mounting of the plunger 4 on the prefilled syringe body 10 finishes.

As described above, in this prefilled syringe, by performing the operation of rotating the plunger 4, the engaging portion 41 of the mounting distal part 40 of the plunger 4 and the engaging rib 76 of the plunger-mounting member 7 engage each other. Thus an operator can confirm through a bodily sensation during the plunger-mounting work that the engaging rib of the plunger-mounting part and the engaging portion of the plunger have engaged each other. The plunger 4 mounted on the prefilled syringe body 10 is locked to the engaging rib 76 of the plunger-mounting member 7 in such a way that the plunger 4 does not separate from the prefilled syringe body 10. When the plunger 4 mounted on the prefilled syringe body 10 is rotated, there is a possibility that the plunger-mounting member 7 follows the rotation of the plunger 4. But in the state in which the portion of the distal part 71 of the plunger-mounting member 7 where the spiral ribs are formed is accommodated inside the accommodation part 62 of the gasket body 6, the plunger-mounting member 7 idles. Thus the rotation of the plunger 4 is not transmitted to the gasket body 6.

A prefilled syringe of another embodiment of the present invention is described below with reference to drawings.

Figure 22:
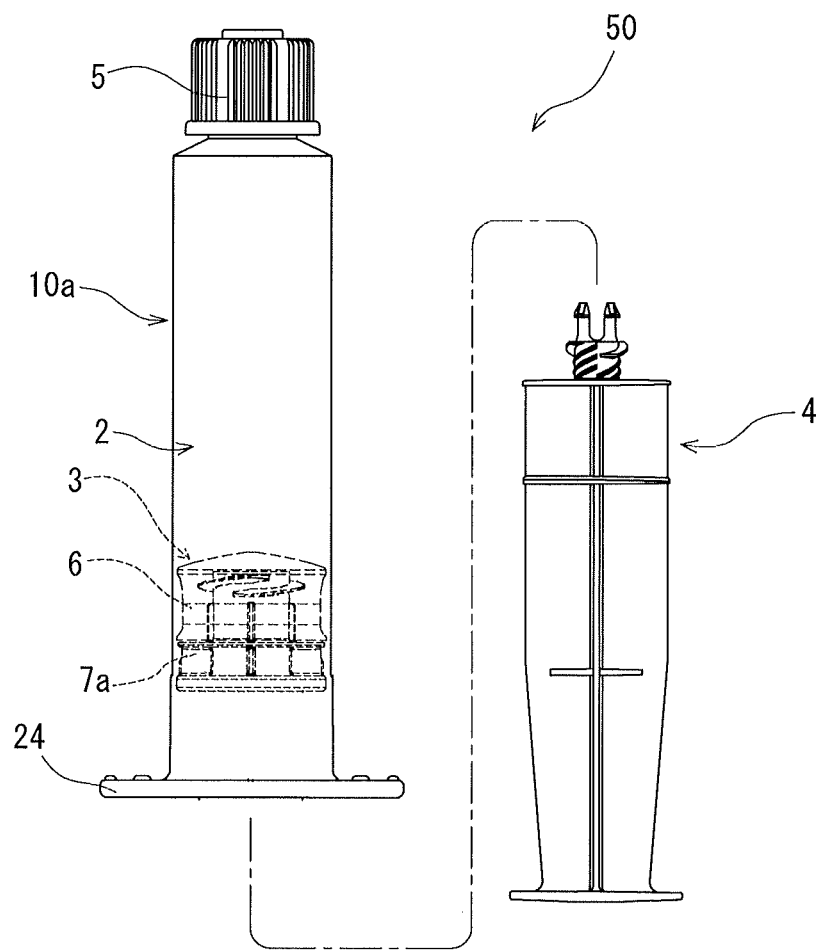
FIG. 22 is a front view of a prefilled syringe of another embodiment of the present invention.
Figure 23:
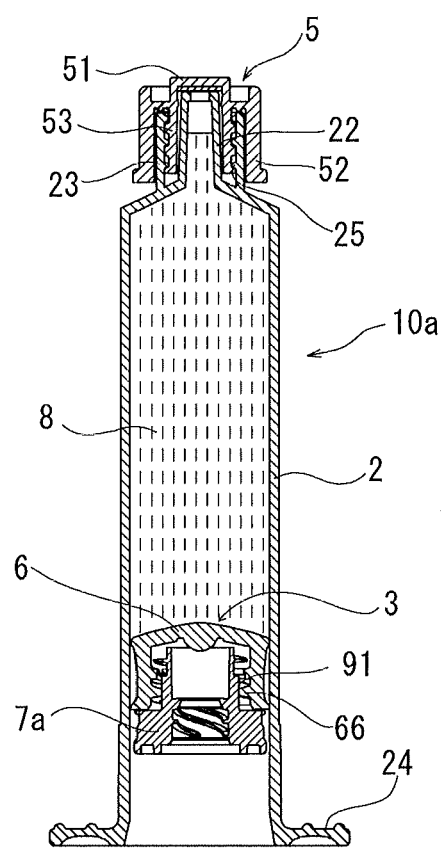
FIG. 23 is a vertical sectional view of a prefilled syringe body of the prefilled syringe shown in FIG. 22.
Figure 24:
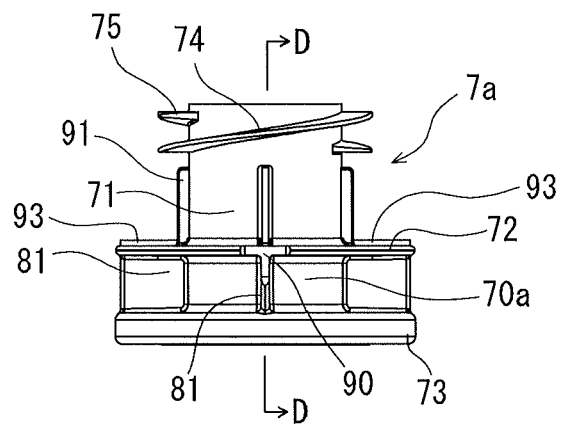
FIG. 24 is a front view of a plunger-mounting member to be used for a gasket shown in FIG. 22.
Figure 25:
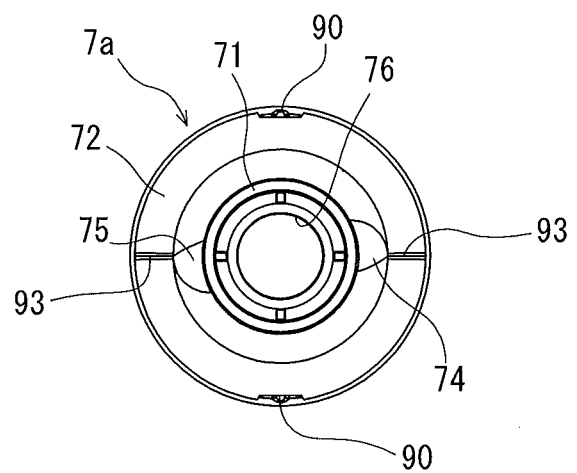
FIG. 25 is a plan view of the plunger-mounting member shown in FIG. 24.
Figure 26:
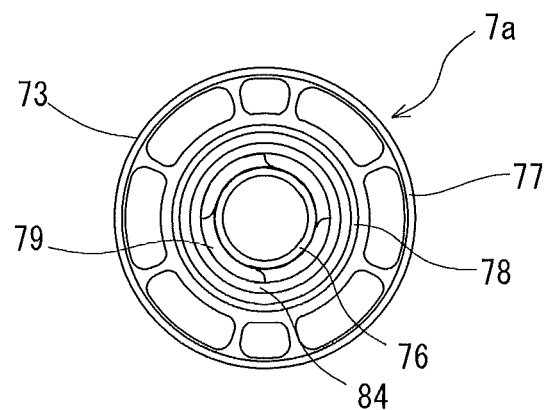
FIG. 26 is a bottom view of the plunger-mounting member shown in FIG. 24.
Figure 27:
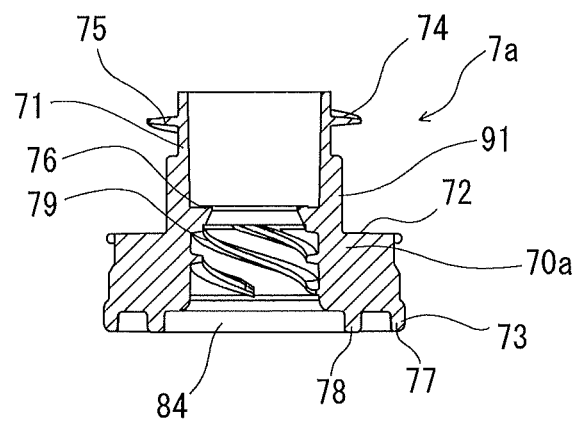
FIG. 27 is a sectional view taken along a line D-D of FIG. 24.
Figure 28:
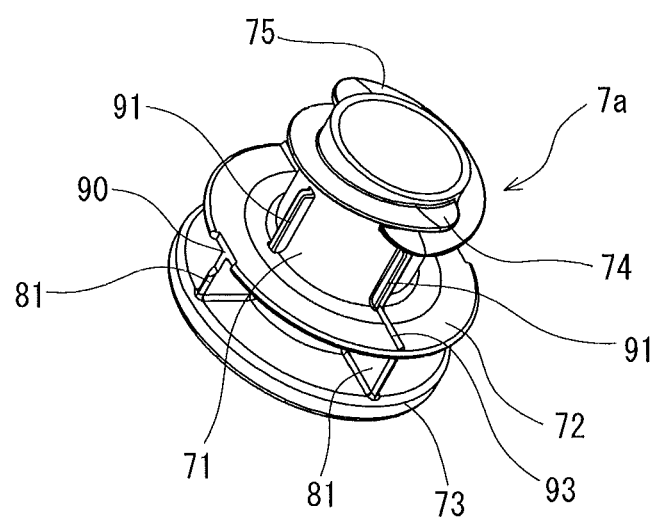
FIG. 28 is a perspective view of the plunger-mounting member shown in FIG. 24.

A prefilled syringe 50 of the embodiment shown in FIGS. 22 and 23 has a prefilled syringe body 10a and the plunger 4 which can be mounted on the prefilled syringe body 10a (gasket 3) and is not mounted thereon.

The prefilled syringe body 10a has the outer cylinder 2, the sealing member 5 for sealing the opening formed at the distal end of the outer cylinder 2, the gasket 3 slidably accommodated inside the outer cylinder 2, and the medicine 8 accommodated inside the medicine accommodation part formed inside the outer cylinder 2. The gasket 3 is composed of the gasket body 6 and a plunger-mounting member 7a mounted on the gasket body 6. The prefilled syringe 50 of this embodiment is different from the above-described prefilled syringe 1 in only the construction of the plunger-mounting member of the gasket 3. Because the gasket body, the outer cylinder, and the plunger of the prefilled syringe 50 are the same as those of the prefilled syringe 1, only the plunger-mounting member 7a is described below.

In the prefilled syringe 50 of this embodiment, the gasket 3 is located at a position distal from the opening formed at the proximal end of the outer cylinder 2 by a predetermined length. The proximal end of the plunger-mounting member 7a is also located at a position distal from the opening formed at the proximal end of the outer cylinder 2 by a predetermined length. The space between the opening formed at the proximal end of the outer cylinder 2 and the proximal end of the plunger-mounting member 7a is formed as a guide portion for guiding the plunger 4 to the plunger-mounting member 7a.

As shown in FIGS. 23 through 28, the plunger-mounting member 7a is a tubular body, having a predetermined length, which has a hollow part penetrating therethrough from one end thereof to the other end thereof.

Similarly to the above-described embodiment, the plunger-mounting member 7a has the body part 70a, the distal part 71 which is projected distally from the body part 70a and can be accommodated inside the lumen part 60 of the gasket body 6, and the plunger-mounting part, formed inside the proximal portion of the body part 70a, on which the plunger 4 is to be mounted.

The body part 70a is a tubular part having an axially shorter length than the body part 70 of the above-described plunger-mounting member 7 and has the plunger-mounting part at its proximal portion. Similarly to the prefilled syringe 1 of the above-described embodiment, the gasket body 6 is located at the position distal from the opening formed at the proximal end of the outer cylinder 2 by the predetermined length. The proximal end of the plunger-mounting member 7a mounted on the gasket body 6 is also located at the position distal from the opening formed at the proximal end of the outer cylinder 2 by the predetermined length. Because in this embodiment, the proximal portion of the outer cylinder 2 constructs the guide portion for guiding the plunger 4 to the plunger-mounting member 7a, the operation of mounting the plunger 4 on the plunger-mounting member 7a can be preferably performed. The length of the guide portion (the distance between the opening formed at the proximal end of the outer cylinder 2 and the proximal end of the plunger-mounting member 7a) is preferably 15 to 40 mm and especially preferably 20 to 30 mm.

The tubular body part 70a has a plurality of the side plate portions 81 axially extended on its side surface. The body part 70a has the disk-shaped distal side flange part 72 capable of pressing the proximal end surface of the gasket body 6 at its distal end. The body part 70a has the disk-shaped proximal side flange part 73 capable of contacting the pressing part 48 of the plunger 4 at its proximal end. A plurality of the side plate portions 81 connects the distal side flange part 72 and the proximal side flange part 73 to each other and reinforces both flange parts 72 and 73.

The outer edge of the distal side flange part 72 is almost circular. The outer diameter of the distal side flange part 72 is set a little smaller than that of the proximal end of the gasket body 6. The peripheral portion of the distal side flange part 72 at its distal side is formed as a substantial flat surface which contacts and is capable of pressing the proximal end surface of the gasket body 6. In this embodiment, as shown in FIGS. 23 through 28, the proximal side flange part 73 has a flat plate portion and a collar portion extended by a predetermined length from the flat plate portion toward the proximal end of the plunger-mounting member 7a. In the plunger-mounting member 7a of this embodiment, the proximal side flange part 73 has the outer collar 77 and the inner collar 78 both extended a little from the flat plate portion toward the proximal end of the plunger-mounting member 7a. The outer collar 77 and the inner collar 78 are concentrically formed. The distal end (free end) of the outer collar 77 and that of the inner collar 78 are formed flatly. The distal end (free end) of the inner collar 78 is projected a little beyond the distal end of the outer collar 77.

The distal part 71 projected from the body part 70a is a cylindrical part which has an almost equal outer diameter and a predetermined length. The distal part 71 is formed longer than the body part 70a. The distal part 71 is projected distally from the vicinity of the center of the distal side flange part 72 of the body part 70a. In a normal state of the gasket body 6, namely, in a state in which the gasket body 6 does not deform, the distal part 71 does not contact the inner surface of the distal portion of the gasket body 6.

The spiral ribs 74, 75 are formed on the outer surface of the distal portion of the distal part 71 of the plunger-mounting member 7a. As shown in FIGS. 22, 24, 25, 27 and 28, in the plunger-mounting member 7a of this embodiment, in correspondence to the spiral screwing part 63 of the gasket body 6, two lines of the spiral ribs 74, 75 are formed. Each of the spiral ribs 74, 75 has a start point located at a position in the vicinity of the distal end of the distal part 71 of the plunger-mounting member 7a and is extended toward the proximal end of the distal part 71 by a predetermined length. Although it is preferable that the plunger-mounting member 7a has a plurality of the spiral ribs (specifically, two lines), the spiral rib may be composed of only one line (one piece).

It is preferable that the height of the annular projected part of the gasket body 6 and that of the spiral rib of the plunger-mounting member 7a are set as follows: The height of the annular projected part of the gasket body 6 is favorably 1.0 to 3.0 mm and more favorably 1.5 to 2.5 mm. The height of the spiral rib of the plunger-mounting member 7a is favorably 2.5 to 3.2 mm, more favorably 2.8 to 3.1 mm, and most favorably 2.95 to 3.05 mm. The width of a contact portion of the annular projected part and a contact portion of the spiral rib is favorably 0.5 to 2.5 mm and especially favorably 1.0 to 2.3 mm. The inner diameter of the annular projected part of the gasket body 6 is favorably 16.0 to 20.0 mm and especially favorably 17.0 to 19.0 mm. The outer diameter of the spiral rib of the plunger-mounting member 7a is favorably 19.0 to 22.0 mm and especially favorably 20.0 to 21.0 mm.

In the prefilled syringe of this embodiment, similarly to the above-described embodiment, the gasket body 6 has the spiral projection 66 for forming the spiral screwing part 63. Further the plunger-mounting member 7a has a rib, formed on the outer surface of the distal part 71 that can be accommodated inside the lumen part 60 of the gasket body 6, which contacts the spiral projection 66 of the gasket body 6 in mounting the plunger-mounting member 7a on the gasket body 6, thus constituting a resistance to the rotation of the plunger-mounting member 7a inside the gasket body 6.

Figure 29:
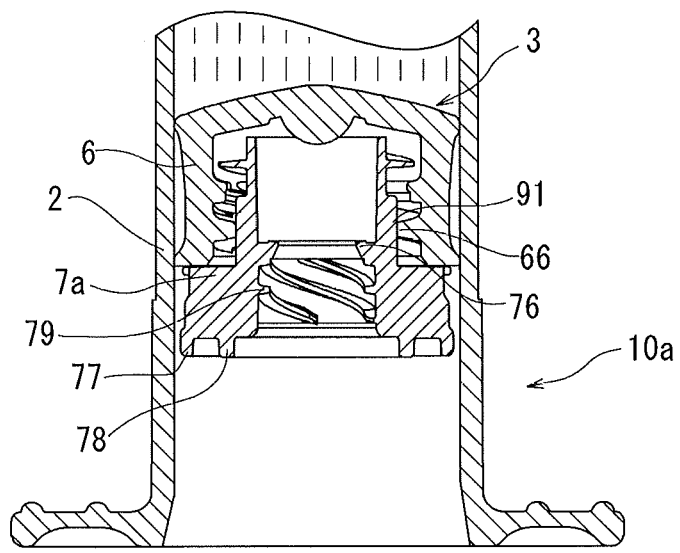
FIG. 29 is an explanatory view for explaining an action in mounting the plunger on the prefilled syringe body of the prefilled syringe of the embodiment shown in FIGS. 22 and 23.
Figure 29:
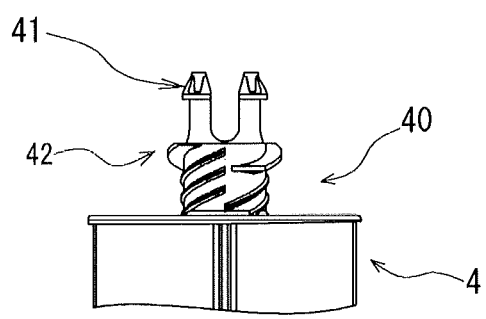

The plunger-mounting member 7a of this embodiment has an axial rib 91 formed on a side surface of the tubular distal part 71 at a position thereof proximal from the portion thereof where the spiral ribs 74, 75 are formed. In this embodiment, a plurality of the axial ribs 91 is formed. In the case where a plurality of the axial ribs 91 is formed, it is preferable to dispose the axial ribs 91 in such a way that they form an almost equal angle with the axis of the distal part 71. As shown in FIGS. 23 and 29, the axial rib 91 contacts (contacts at a higher frictional force than a predetermined frictional force) the spiral projection 66 formed on the inner surface of the gasket body 6, thus preventing the plunger-mounting member 7a from idling with respect to the gasket body 6. More specifically, in mounting the plunger-mounting member 7a on the gasket body 6, the axial rib 91 of the plunger-mounting member 7a presses the spiral projection 66 of the gasket body 6 a little. In this embodiment, the axial rib 91 is extended from the distal side flange part 72 toward the distal end of the plunger-mounting member 7a and in parallel with the axis of the plunger-mounting member 7a and terminates at a position of the tubular distal part 71 located a little proximally from the portion thereof where the spiral ribs 74, 75 are formed.

The height of the axial rib 91 of the plunger-mounting member 7a is preferably 0.5 to 2 mm. The number of the axial ribs 91 is favorably two to eight and especially favorably three to six. The diameter of a circle which passes the outer surface of the axial rib 91 of the plunger-mounting member 7a is favorably a little larger and more favorably 1 to 2 mm larger than the diameter of a circle which passes the outer surface of the spiral projection 66 of the gasket body 6.

In the plunger-mounting member 7a of this embodiment, on the distal end surface of the distal side flange part 72, there is formed a rib 93 which is extended toward the center of the plunger-mounting member 7a from the peripheral edge of the distal end surface of the distal side flange part 72 and reaches the above-described axial rib 91. Two ribs 93 are formed by opposing them to each other. In mounting the plunger on the gasket with the plunger being pressed, the rib 93 is pressed against the gasket. Thereby the plunger-mounting member is prevented from idling with respect to the gasket.

In the plunger-mounting member 7a of this embodiment, a concave portion 90 is formed on a side surface of the distal side flange part 72. Two concave portions 90 are formed by opposing them to each other.

Similarly to the above-described plunger-mounting member 7, the plunger-mounting part for accommodating the mounting distal part 40 of the plunger 4 therein and mounting the mounting distal part 40 thereon is formed on the inner surface of the hollow part of the plunger-mounting member 7a. The plunger-mounting part has the spiral concave portion 79 on which the spiral projected portion 42 (42a, 42b) of the mounting distal part 40 is to screw and the engaging rib 76, located at a position in the vicinity of the spiral concave portion 79 and distal therefrom, which is to engage the engaging portion 41 of the mounting distal part 40. As shown in FIGS. 24 through 28, the plunger-mounting member 7a has the large-diameter opening 84 at its proximal end. The spiral concave portion 79 is formed on the inner surface of a lumen part having a smaller diameter than the large-diameter opening 84. The spiral concave portion 79 has a start point located at a position a little distal from the opening formed at the proximal end of the plunger-mounting member 7a and is extended toward the distal side of the plunger-mounting member 7a by a predetermined length. The spiral concave portion 79 is composed of two lines (two pieces). Although it is preferable that the plunger-mounting member 7a has the spiral concave portion composed of a plurality of lines (specifically, two lines), the spiral concave portion may be composed of only one line (one piece).

The plunger-mounting part has the engaging rib 76 located at a position in the vicinity of the spiral concave portion 79 and distal therefrom. The engaging rib 76 engages the engaging portion 41 of the mounting distal part 40 of the plunger 4 to be described later. The inner surface of the engaging rib 76 forms the annular tapered configuration which tapers such that the inner diameter of the engaging rib 76 becomes gradually smaller toward the distal end of the plunger-mounting member 7a. This construction allows the engaging portion 41 of the plunger 4 to be described later to easily enter the plunger-mounting part and pass therethrough. The distal end surface of the engaging rib 76 is formed erectly from the body part 70, in other words, as an annular flat surface almost orthogonal to the axis of the body part 70a. Therefore the engaging rib 76 which has engaged the engaging portion 41 of the plunger 4 to be described later is prevented from separating therefrom. Although it is preferable that the engaging rib 76 is annular, the engaging rib 76 may be dashed line-shaped (uncontinuous).

As the material for forming the plunger-mounting member 7a, it is preferable to use hard or semi-hard resin such as high-density polyethylene, polypropylene, polystyrene, and polyethylene terephthalate.

As shown in FIGS. 23 and 29, in the prefilled syringe 50 of this embodiment, the outer cylinder 2 also accommodates the gasket 3 having the gasket body 6 on which the plunger-mounting member 7a is mounted. The proximal end of the plunger-mounting member 7a is not substantially projected beyond the proximal end of the outer cylinder 2, but is located at a position distal from the proximal end of the outer cylinder 2 by a predetermined length. The plunger-mounting member 7a is mounted on the gasket body 6, as described below.

After the spiral ribs 74, 75 of the plunger-mounting member 7a are inserted into the gasket body 6 from the start point of the spiral screwing part 63, the plunger-mounting member 7a is rotated. Thereby screwing between the spiral screwing part 63 and the spiral ribs 74, 75 progresses. During the progress of the screwing therebetween, the axial rib 91 of the plunger-mounting member 7a proceeds with the axial rib 91 pressing the spiral projection 66 of the gasket body 6 a little and sliding in contact therewith. During the progress of the screwing, the start points of the spiral ribs 74, 75 of the plunger-mounting member 7a approach the termination point of the spiral screwing part 63 of the gasket body 6 and the rib-absent portion 65 of the annular projected part 64 thereof and are positioned between the spiral projection 66 forming the spiral screwing part 63 and the annular projected part 64. By further rotating the plunger-mounting member 7a, the spiral ribs 74, 75 pass the rib-absent portion 65 of the annular projected part 64 and enter the accommodation part 62. By continuing to rotate the plunger-mounting member 7a, as shown in FIG. 23, the spiral ribs 74, 75 entirely pass the rib-absent portion 65 of the annular projected part 64, and the portion of the distal part 71 of the plunger-mounting member 7a where the spiral ribs 74, 75 are formed is accommodated inside the accommodation part 62 of the gasket body 6. The axial rib 91 of the plunger-mounting member 7a maintains a state in which the axial rib 91 presses the spiral projection 66 of the gasket body 6 a little. Thereby the work of mounting the plunger-mounting member 7a on the gasket body 6 finishes.

Figure 30:
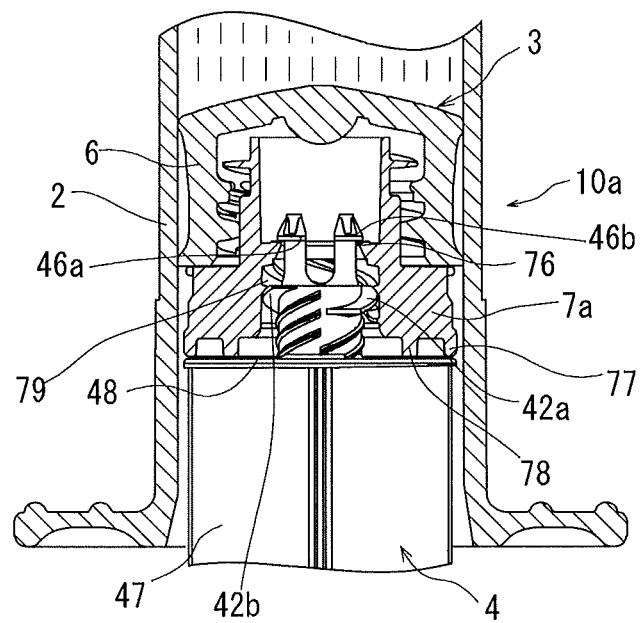
FIG. 30 is an explanatory view for explaining the action in mounting the plunger on the prefilled syringe body of the prefilled syringe of the embodiment shown in FIGS. 22 and 23.

The action of the prefilled syringe 50 of this embodiment is described below with reference to FIGS. 29 and 30.

In the prefilled syringe body 10a, the gasket 3 is accommodated inside the outer cylinder 2 at a position distal from the proximal end of the outer cylinder 2 by a predetermined length. As shown in FIG. 29, the plunger 4 is entered into the outer cylinder 2 from the opening formed at the proximal end thereof and thereafter into the hollow part of the plunger-mounting member 7a with the plunger 4 being rotated. Thereby the spiral projected portion 42 (42a, 42b) of the mounting distal part 40 of the plunger 4 screws the spiral concave portion 79 of the plunger-mounting part of the plunger-mounting member 7a. During the progress of the screwing therebetween, the engaging portion 41 of the mounting distal part 40 of the plunger 4 proceeds toward the engaging rib 76 of the plunger-mounting member 7a. As a result, the convex portions 46a, 46b, 46c, and 46d of the claw portions 43a, 43b, 43c, and 43d of the plunger 4 ride across the engaging rib 76 of the plunger-mounting member 7a. Thereafter as shown in FIG. 30, the convex portions 46a, 46b, 46c, and 46d engage the engaging rib 76 of the plunger-mounting member 7a. In this manner, the mounting of the plunger 4 on the prefilled syringe body 10a finishes.

As described above, because in the prefilled syringe 50 of this embodiment, initially, the plunger 4 is inserted into the outer cylinder 2, the plunger 4 reaches the plunger-mounting member 7a with the plunger 4 being almost parallel with the axis of the outer cylinder. Thus it is possible to mount the plunger 4 on the plunger-mounting member 7a securely and in a preferable state. Further by performing the operation of rotating the plunger 4, the engaging portion 41 of the mounting distal part 40 of the plunger 4 and the engaging rib 76 of the plunger-mounting member 7a engage each other. Thus an operator can confirm through a bodily sensation during the plunger-mounting work that the engaging rib of the plunger-mounting part and the engaging portion of the plunger have engaged each other. The plunger mounted on the prefilled syringe body 10a is locked to the engaging rib 76 of the plunger-mounting member 7a in such a way that the plunger 4 does not separate from the prefilled syringe body 10a. When the gap between the inner diameter of the outer cylinder and the shaft part 47 as well as the pressing part 48 is small, position adjustment in the engagement can be accomplished securely.

Figure 31:
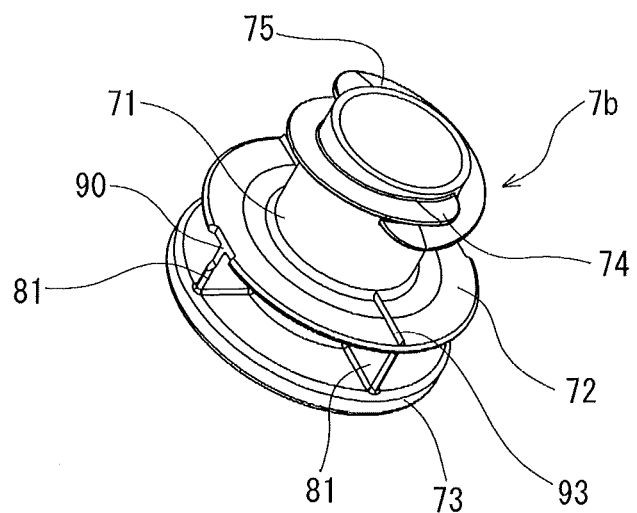
FIG. 31 is a perspective view of a plunger-mounting member to be used for a prefilled syringe of another embodiment of the present invention.
Figure 32:
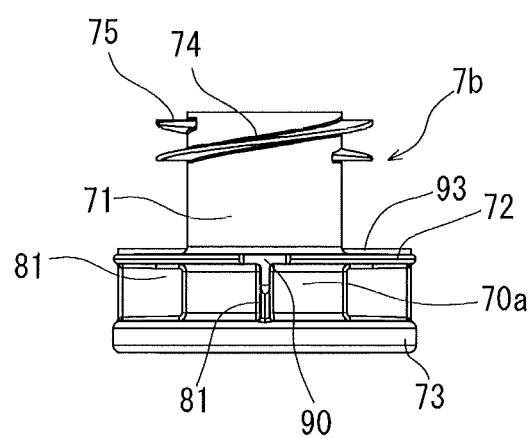
FIG. 32 is a front view of the plunger-mounting member shown in FIG. 31.

The plunger-mounting member may have a construction as shown in FIGS. 31 and 32.

The only difference between a plunger-mounting member 7b of this embodiment and the above-described plunger-mounting member 7a is that the latter has the axial rib 91 on the side surface of the tubular distal part 71, whereas the former does not have the axial rib 91 thereon.

Figure 33:
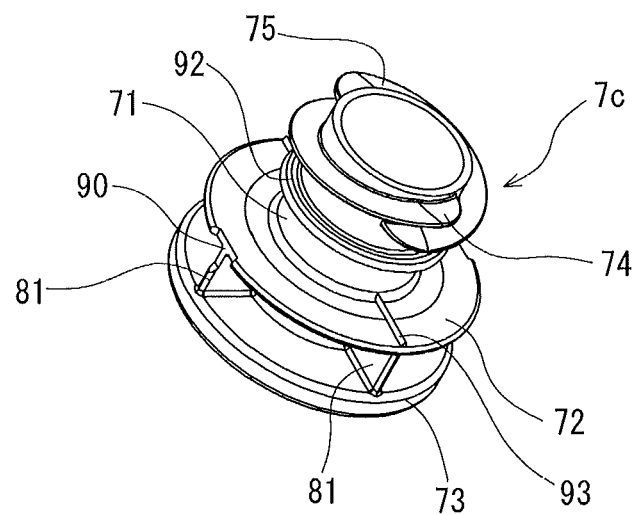
FIG. 33 is a perspective view of a plunger-mounting member to be used for a prefilled syringe of another embodiment of the present invention.
Figure 34:
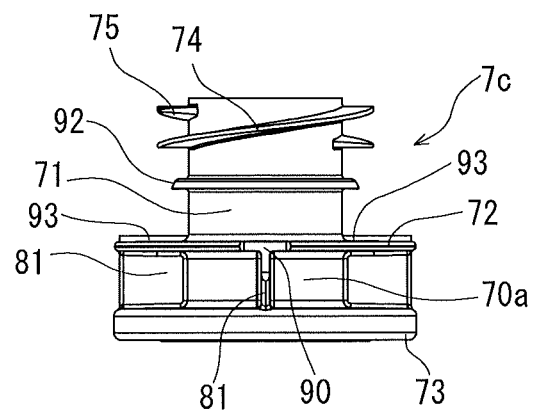
FIG. 34 is a front view of the plunger-mounting member shown in FIG. 33.

The plunger-mounting member may have a construction as shown in FIGS. 33 and 34.

The above-described plunger-mounting member 7a has the axial rib. A plunger-mounting member 7c of this embodiment does not have the axial rib, but has an annular rib 92 on the side surface of the tubular distal part 71.

The plunger-mounting member 7c of this embodiment has the annular rib 92 formed on the side surface of the tubular distal part 71 at a position thereof proximal from the portion thereof where the spiral ribs 74, 75 are formed. The annular rib 92 is formed endlessly and orthogonally to the axis of the plunger-mounting member 7c. The annular rib 92 contacts (contacts at a higher frictional force than a predetermined frictional force) the spiral projection 66 formed on the inner surface of the gasket body 6, thus preventing the plunger-mounting member 7c from idling with respect to the gasket body 6. More specifically, in mounting the plunger-mounting member 7e on the gasket body 6, the annular rib 92 of the plunger-mounting member 7c presses the spiral projection 66 of the gasket body 6 a little.

The height of the annular rib 92 of the plunger-mounting member 7c is preferably 0.5 to 2 mm. The outer diameter of the annular rib 92 of the plunger-mounting member 7c is favorably a little larger and especially favorably 1 to 2 mm larger than the diameter of a circle which passes the outer surface of the spiral projection 66 of the gasket body 6.

Figure 35:
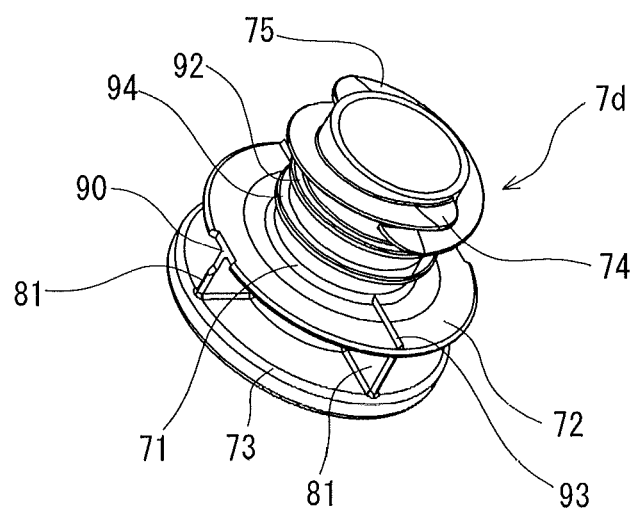
FIG. 35 is a perspective view of a plunger-mounting member to be used for a prefilled syringe of another embodiment of the present invention.
Figure 36:
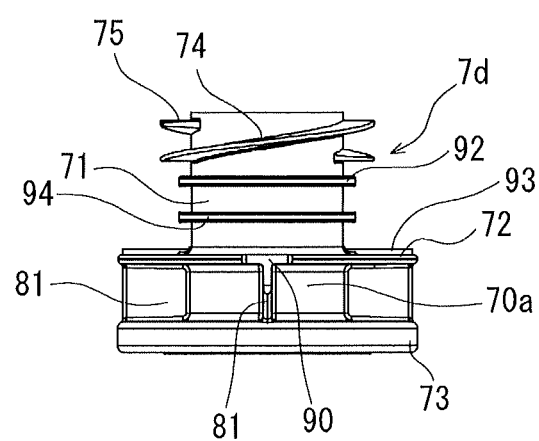
FIG. 36 is a front view of the plunger-mounting member shown in FIG. 35.

The plunger-mounting member may have a construction as shown in FIGS. 35 and 36.

The above-described plunger-mounting member 7a has the axial rib. A plunger-mounting member 7d of this embodiment does not have the axial rib, but has a first annular rib 92 and a second annular rib 94 on the side surface of the tubular distal part 71.

More specifically, the plunger-mounting member 7d of this embodiment has the first annular rib 92 formed on the side surface of the tubular distal part 71 at a position thereof proximal from the portion thereof where the spiral ribs 74, 75 are formed. The first annular rib 92 is formed endlessly and orthogonally to the axis of the plunger-mounting member 7d. The first annular rib 92 contacts (contacts at a higher frictional force than a predetermined frictional force) the spiral projection 66 formed on the inner surface of the gasket body 6, thus preventing the plunger-mounting member 7d from idling with respect to the gasket body 6. More specifically, in mounting the plunger-mounting member 7d on the gasket body 6, the first annular rib 92 of the plunger-mounting member 7d presses the spiral projection 66 of the gasket body 6 a little.

The plunger-mounting member 7d of this embodiment has the second annular rib 94 formed on the side surface of the tubular distal part 71 at a portion thereof located between the above-described first annular rib 92 formed on the tubular distal part 71 and the distal side flange part 72. The second annular rib 94 is formed endlessly and orthogonally to the axis of the plunger-mounting member 7d. The second annular rib 94 contacts (contacts at a higher frictional force than a predetermined frictional force) the spiral projection 66 formed on the inner surface of the gasket body 6, thus preventing the plunger-mounting member 7d from idling with respect to the gasket body 6. More specifically, in mounting the plunger-mounting member 7d on the gasket body 6, the second annular rib 94 of the plunger-mounting member 7d presses the spiral projection 66 of the gasket body 6 a little.

The height of the first annular rib 92 of the plunger-mounting member 7d and that of the second annular rib 94 thereof are preferably 0.5 to 2 mm. The outer diameter of the first annular rib 92 of the plunger-mounting member 7d and that of the second annular rib 94 thereof are favorably a little larger and especially favorably 1 to 2 mm larger than the diameter of the circle which passes the outer surface of the spiral projection 66 of the gasket body 6. Unlike the above-described embodiments, the number of the annular rib is not limited to one or two, but may be not less than three and favorably one to three.

Figure 37:
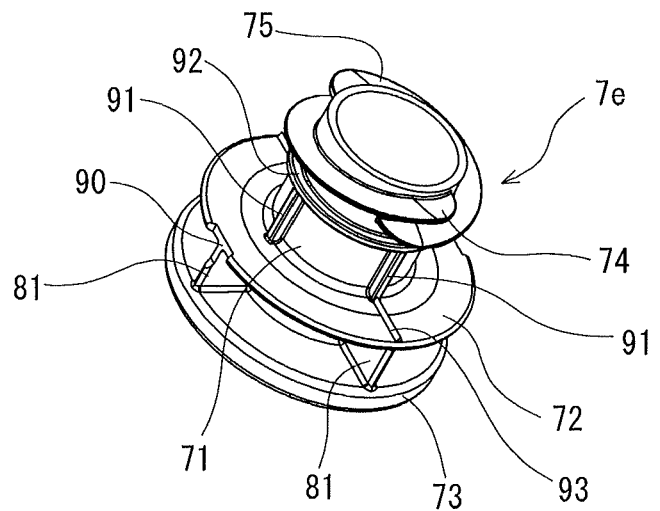
FIG. 37 is a perspective view of a plunger-mounting member to be used for a prefilled syringe of another embodiment of the present invention.
Figure 38:
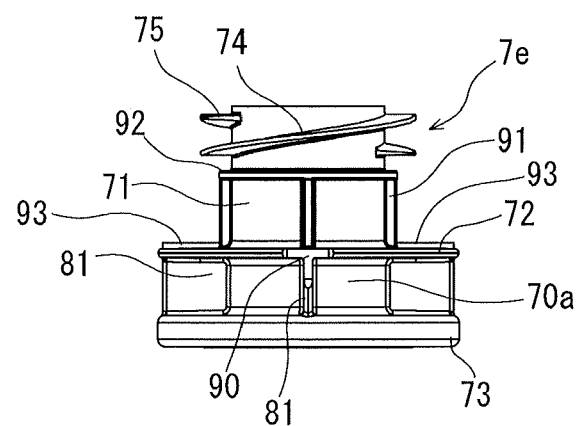
FIG. 38 is a front view of the plunger-mounting member shown in FIG. 37.

The plunger-mounting member may have a construction as shown in FIGS. 37 and 38.

The only difference between a plunger-mounting member 7e of this embodiment and the above-described plunger-mounting member 7a is that the former has the annular rib 92 formed on the side surface of the tubular distal part 71.

Similarly to the plunger-mounting member 7a, the plunger-mounting member 7e of this embodiment has the axial rib 91 formed on the side surface of the tubular distal part 71 at a position thereof proximal from the portion where the spiral ribs 74, 75 are formed. In this embodiment, a plurality of the axial ribs 91 is formed. In the case where a plurality of the axial ribs 91 is formed, it is preferable to dispose the axial ribs 91 in such a way that they form an almost equal angle with the axis of the distal part 71. As shown in FIGS. 37 and 38, the axial rib 91 contacts (contacts at a higher frictional force than a predetermined frictional force) the spiral projection 66 formed on the inner surface of the gasket body 6, thus preventing the plunger-mounting member 7e from idling with respect to the gasket body 6. More specifically, in mounting the plunger-mounting member 7e on the gasket body 6, the axial rib 91 of the plunger-mounting member 7e presses the spiral projection 66 of the gasket body 6 a little. In this embodiment, the axial rib 91 is extended from the distal side flange part 72 toward the distal end of the plunger-mounting member 7e and in parallel with the axis of the plunger-mounting member 7e and terminates at a position of the distal part 71a little proximal from the portion thereof where the spiral ribs 74, 75 are formed.

The plunger-mounting member 7e of this embodiment has the annular rib 92 formed on the side surface of the tubular distal part 71 at a position thereof proximal from the portion thereof where the spiral ribs 74, 75 are formed. The annular rib 92 is formed endlessly and orthogonally to the axis of the plunger-mounting member 7e. In this embodiment, the annular rib 92 is continuous with the termination points of a plurality of the axial ribs 91. The annular rib 92 also contacts (contacts at a higher frictional force than a predetermined frictional force) the spiral projection 66 formed on the inner surface of the gasket body 6, thus preventing the plunger-mounting member 7e from idling with respect to the gasket body 6. More specifically, in mounting the plunger-mounting member 7e on the gasket body 6, the annular rib 92 of the plunger-mounting member 7e presses the spiral projection 66 of the gasket body 6 a little.

The height of the annular rib 92 of the plunger-mounting member 7e is preferably 0.5 to 2 mm. The outer diameter of the annular rib 92 of the plunger-mounting member 7e is favorably a little larger and especially favorably 1 to 2 mm larger than the diameter of a circle which passes the outer surface of the spiral projection 66 of the gasket body 6.

Figure 39:
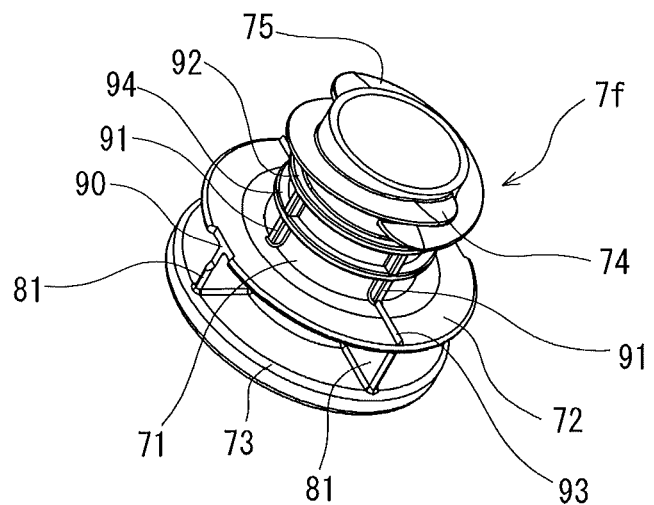
FIG. 39 is a perspective view of a plunger-mounting member to be used for a prefilled syringe of another embodiment of the present invention.
Figure 40:
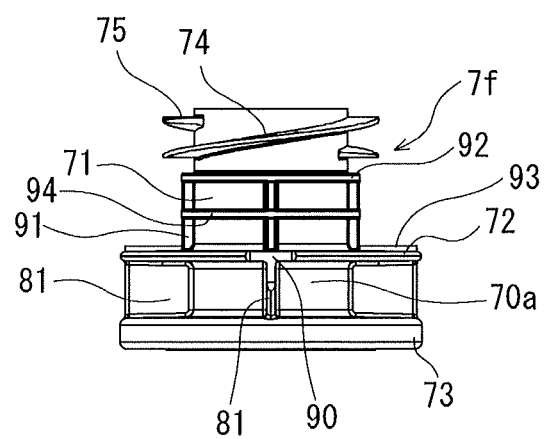
FIG. 40 is a front view of the plunger-mounting member shown in FIG. 39.
Figure 41:
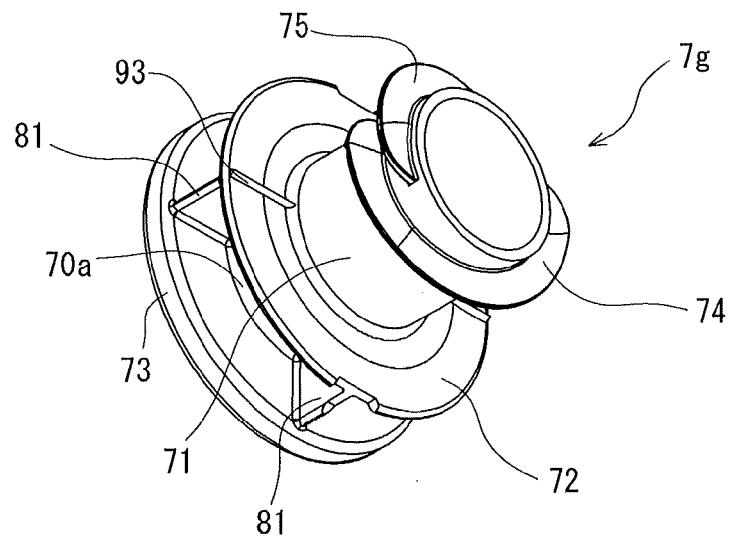
FIG. 41 is a perspective view of a plunger-mounting member to be used for a prefilled syringe of another embodiment of the present invention.

The plunger-mounting member may have a construction as shown in FIGS. 39 and 40.

The only difference between a plunger-mounting member 7f of this embodiment and the above-described plunger-mounting member 7a is that the former has the first annular rib 92 and the second annular rib 94 formed on the side surface of the tubular distal part 71.

Similarly to the plunger-mounting member 7a, the plunger-mounting member 7f of this embodiment has the axial rib 91 formed on the side surface of the tubular distal part 71 at a position thereof proximal from the portion thereof where the spiral ribs 74, 75 are formed. In this embodiment, a plurality of the axial ribs 91 is formed. In the case where a plurality of the axial ribs 91 is formed, it is preferable to locate the axial ribs 91 in such a way that they form an almost equal angle with the axis of the distal part 71. As shown in FIGS. 39 and 40, the axial rib 91 contacts (contacts at a higher frictional force than a predetermined frictional force) the spiral projection 66 formed on the inner surface of the gasket body 6, thus preventing the plunger-mounting member 7f from idling with respect to the gasket body 6. More specifically, in mounting the plunger-mounting member 7f on the gasket body 6, the axial rib 91 of the plunger-mounting member 7f presses the spiral projection 66 of the gasket body 6 a little. In this embodiment, the axial rib 91 is extended from the distal side flange part 72 toward the distal end of the plunger-mounting member 7f and in parallel with the axis of the plunger-mounting member 7f and terminates at a position of the distal part 71a little proximal from the portion where the spiral ribs 74, 75 are formed.

The plunger-mounting member 7f of this embodiment has the first annular rib 92 formed on the side surface of the tubular distal part 71 at a position thereof proximal from the portion thereof where the spiral ribs 74, 75 are formed. The first annular rib 92 is formed endlessly and orthogonally to the axis of the plunger-mounting member 7f. In this embodiment, the first annular rib is continuous with the termination points of a plurality of the axial ribs 91. The first annular rib 92 also contacts (contacts at a higher frictional force than a predetermined frictional force) the spiral projection 66 formed on the inner surface of the gasket body 6, thus preventing the plunger-mounting member 7f from idling with respect to the gasket body 6. More specifically, in mounting the plunger-mounting member 7f on the gasket body 6, the first annular rib 92 of the plunger-mounting member 7f presses the spiral projection 66 of the gasket body 6 a little.

The plunger-mounting member 7f of this embodiment has the second annular rib 94 formed on the side surface of the tubular distal part 71 at a portion thereof located between the above-described first annular rib 92 formed on the tubular distal part 71 and the distal side flange part 72. The second annular rib 94 is formed endlessly and orthogonally to the axis of the plunger-mounting member 7f. In this embodiment, the second annular rib 94 is continuous with intermediate portions of a plurality of the axial ribs 91. The second annular rib 94 also contacts (contacts at a higher frictional force than the predetermined frictional force) the spiral projection 66 formed on the inner surface of the gasket body 6, thus preventing the plunger-mounting member 7f from idling with respect to the gasket body 6. More specifically, in mounting the plunger-mounting member 7f on the gasket body 6, the second annular rib 94 of the plunger-mounting member 7f presses the spiral projection 66 of the gasket body 6 a little. The height of the first annular rib 92 of the plunger-mounting member 7f and that of the second annular rib 94 thereof are preferably 0.5 to 2 mm. The outer diameter of the first annular rib 92 of the plunger-mounting member 7f and that of the second annular rib 94 thereof are favorably a little larger and especially favorably 1 to 2 mm larger than the diameter of the circle which passes the outer surface of the spiral projection 66 of the gasket body 6.

The plunger-mounting member may have a construction as shown in FIGS. 41 through 49.

As shown in FIGS. 41 through 49, a plunger-mounting member 7g is a tubular body, having a predetermined length, which has a hollow part penetrating therethrough from one end thereof to the other end thereof.

Similarly to the above-described plunger-mounting members 7, 7a, and 7b, the plunger-mounting member 7g has the body part 70a, the distal part 71 which is projected distally from the body part 70a and can be accommodated inside the lumen part of the gasket body 6, and the plunger-mounting part, formed inside the proximal portion of the body part 70a, on which the plunger 4 is to be mounted.

The body part 70a is a tubular part having an axially shorter predetermined length than the body part 70 of the above-described plunger-mounting member 7 and has the plunger-mounting part at its proximal portion. Similarly to the prefilled syringe 1 of the above-described embodiment, the gasket body 6 is located at a position distal by a predetermined length from the opening formed at the proximal end of the outer cylinder 2. The proximal end of the plunger-mounting member 7g mounted on the gasket body 6 is also located at a position distal by a predetermined length from the opening formed at the proximal end of the outer cylinder 2. Because in the prefilled syringe of this embodiment, the proximal portion of the outer cylinder 2 constructs the guide portion for guiding the plunger 4 to the plunger-mounting member 7g, the operation of mounting the plunger 4 on the plunger-mounting member 7g can be preferably performed.

The length of the guide portion (the distance between the opening formed at the proximal end of the outer cylinder 2 and the proximal end of the plunger-mounting member 7g) is preferably 15 to 40 mm and especially preferably 20 to 30 mm.

The tubular body part 70a has a plurality of side plate portions 81 axially extended on its side surface. The body part 70a has the disk-shaped distal side flange part 72 capable of pressing the proximal end surface of the gasket body 6 at the distal end thereof. The body part 70a has the disk-shaped proximal side flange part 73 capable of contacting the pressing part 48 of the plunger 4 at its proximal end. A plurality of the side plate portions 81 connects the distal side flange part 72 and the proximal side flange part 73 to each other and reinforces both flange parts 72 and 73.

The outer edge of the distal side flange part 72 is almost circular. The outer diameter of the distal side flange part 72 is set a little smaller than that of the proximal end of the gasket body 6. The peripheral portion of the distal side flange part 72 at its distal end is formed as an almost flat surface which contacts and is capable of pressing the proximal end surface of the gasket body 6. In this embodiment, as shown in FIGS. 41 through 47, the proximal side flange part 73 has a flat plate portion and a collar portion extended by a predetermined length from the flat plate portion toward the proximal end of the plunger-mounting member 7g. In the plunger-mounting member 7g of this embodiment, the proximal side flange part 73 has the outer collar 77 and the inner collar 78 both extended a little from the flat plate portion toward the proximal end of the plunger-mounting member 7g. The outer collar 77 and the inner collar 78 are concentrically formed. The distal end (free end) of the outer collar 77 and that of the inner collar 78 are flat. The distal end (free end) of the inner collar 78 is projected a little beyond the distal end (free end) of the outer collar 77.

The distal part 71 projected from the body part 70a is a cylindrical part which has an almost equal outer diameter and a predetermined length. The distal part 71 is formed longer than the body part 70a. The distal part 71 is projected distally from the vicinity of the center of the distal side flange part 72 of the body part 70a. In a normal state of the gasket body 6, namely, in a state in which the gasket body 6 does not deform, the distal part 71 does not contact the inner surface of the distal part of the gasket body 6.

The spiral ribs 74, 75 are formed on the outer surface of the distal portion of the distal part 71 of the plunger-mounting member 7g. As shown in FIGS. 41 through 45 and 47 through 49, in the plunger-mounting member 7g of this embodiment, in correspondence to the spiral screwing part 63 of the gasket body 6, two lines (two pieces) of the spiral ribs 74, 75 are formed. Each of the spiral ribs 74, 75 has a start point located at a position in the vicinity of the distal end of the distal part 71 of the plunger-mounting member 7g and is extended toward the proximal side of the plunger-mounting member 7g by a predetermined length. Although it is preferable that the plunger-mounting member 7g has a plurality of the spiral ribs (specifically, two lines), the spiral rib may be composed of only one line (one piece).

It is preferable that the height of the annular projected part 64 of the gasket body 6 and that of the spiral rib of the plunger-mounting member 7g are set as follows: The height of the annular projected part 64 of the gasket body is favorably 1.0 to 3.0 mm and more favorably 1.5 to 2.5 mm. The height of the spiral rib of the plunger-mounting member 7g is favorably 2.5 to 3.2 mm, more favorably 2.8 to 3.1 mm, and most favorably 2.95 to 3.05 mm. The inner diameter of the annular projected part 64 of the gasket body 6 is favorably 16.0 to 20.0 mm and especially favorably 17.0 to 19.0 mm. The outer diameter of the spiral rib of the plunger-mounting member 7g is favorably 19.0 to 22.0 mm and especially favorably 20.0 to 21.0 mm.

In the plunger-mounting member 7g of this embodiment, the rib 93 is formed on the distal end surface of the distal side flange part 72. Specifically the rib 93 is extended toward the center of the plunger-mounting member 7g from the peripheral edge of the distal side flange part 72 and reaches the distal part 71. Two ribs 93 are formed by opposing them to each other. In mounting the plunger on the gasket with the plunger being pressed, the rib 93 is pressed against the gasket. Thereby the plunger-mounting member 7g is prevented from idling with respect to the gasket.

Figure 42:
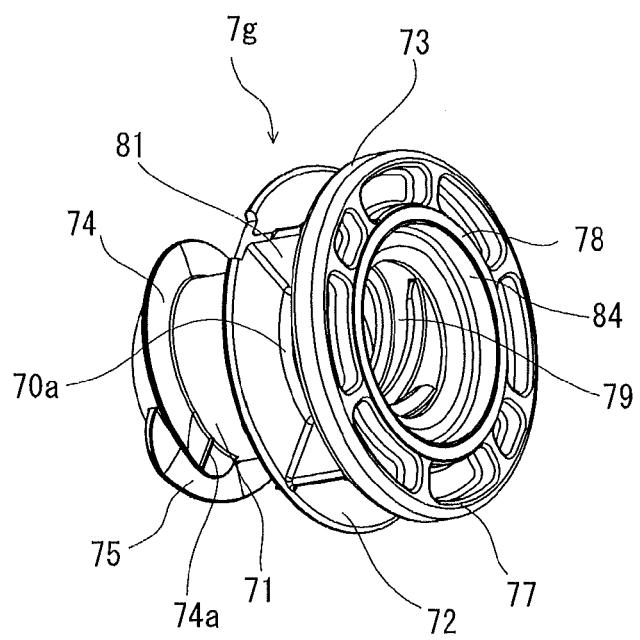
FIG. 42 is a perspective view of the plunger-mounting member shown in FIG. 41 as seen from a bottom surface thereof.
Figure 46:
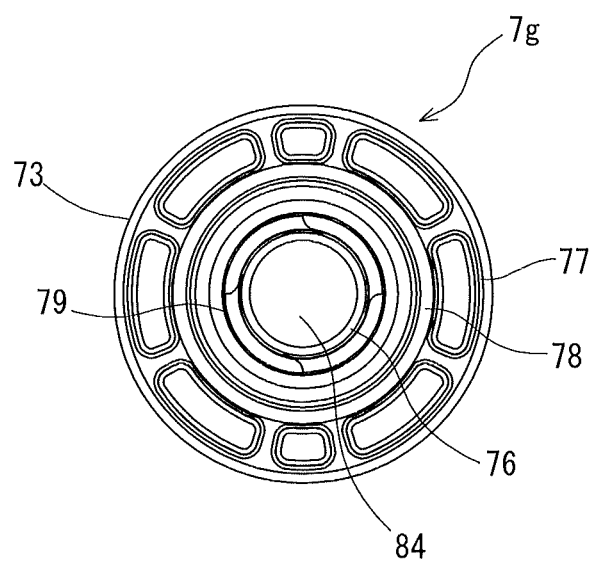
FIG. 46 is a bottom view of the plunger-mounting member shown in FIG. 43.
Figure 47:
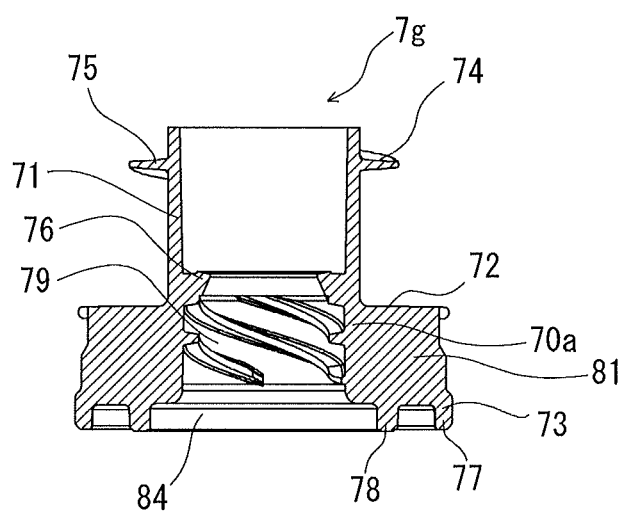
FIG. 47 is a sectional view taken along a line E-E of FIG. 43.

Similarly to the above-described plunger-mounting member 7, the plunger-mounting part for accommodating the mounting distal part 40 of the plunger 4 therein and mounting the mounting distal part 40 thereon is formed on the inner surface of the hollow part of the plunger-mounting member 7g. The plunger-mounting part has the spiral concave portion 79 on which the spiral projected portion 42 (42a, 42b) of the mounting distal part 40 is to screw and the engaging rib 76, located at a position in the vicinity of the spiral concave portion 79 and distal therefrom, which is to engage the engaging portion 41 of the mounting distal part 40. As shown in FIGS. 42, 46, and 47, the plunger-mounting member 7g has the large-diameter opening 84 at its proximal end. The spiral concave portion 79 is formed on the inner surface of a lumen part having a smaller diameter than the large-diameter opening 84. The spiral concave portion 79 has a start point at a position a little distal from the opening formed at the proximal end of the plunger-mounting member 7g and is extended by a predetermined length toward the distal side of the plunger-mounting member 7g. The spiral concave portion 79 is composed of two lines (two pieces). Although it is preferable that the plunger-mounting member 7g has a plurality of lines (specifically, two lines) of the spiral concave portion, the spiral concave portion may be composed of only one line (one piece).

The plunger-mounting part has the engaging rib 76 located at a position in the vicinity of the spiral concave portion 79 and distal therefrom. The engaging rib 76 engages the engaging portion 41 of the mounting distal part 40 of the plunger 4 to be described later. The inner surface of the engaging rib 76 forms the annular tapered surface which tapers such that the diameter becomes gradually smaller toward the distal end of the plunger-mounting member 7a. This construction allows the engaging portion 41 of the plunger 4 to be described later to easily enter the plunger-mounting part and pass therethrough. The distal end surface of the engaging rib 76 is formed erectly from the body part 70, in other words, as an annular flat surface almost orthogonal to the axis of the body part 70a. Therefore the engaging rib 76 which has engaged the engaging portion 41 of the plunger 4 to be described later is prevented from separating therefrom. Although it is preferable that the engaging rib 76 is annular, the engaging rib 76 may be dashed line-shaped (uncontinuous).

As the material for forming the plunger-mounting member 7g, it is preferable to use hard or semi-hard resin such as high-density polyethylene, polypropylene, polystyrene, and polyethylene terephthalate.

Figure 43:
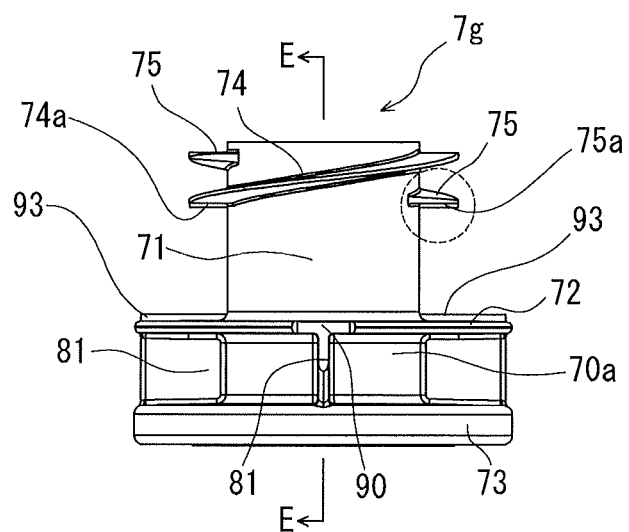
FIG. 43 is a front view of the plunger-mounting member shown in FIG. 41.
Figure 44:
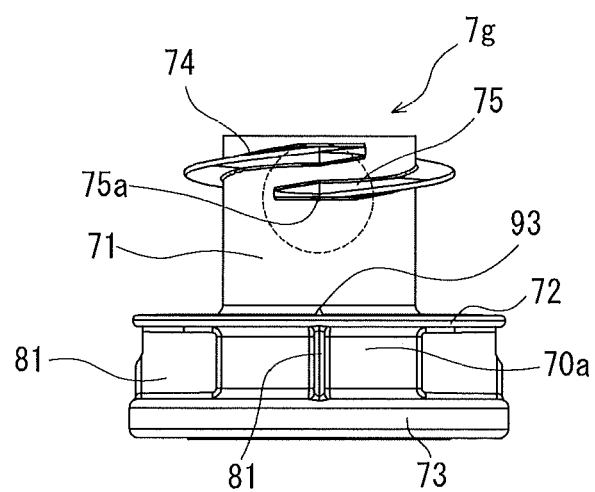
FIG. 44 is a right side view of the plunger-mounting member shown in FIG. 43.
Figure 45:
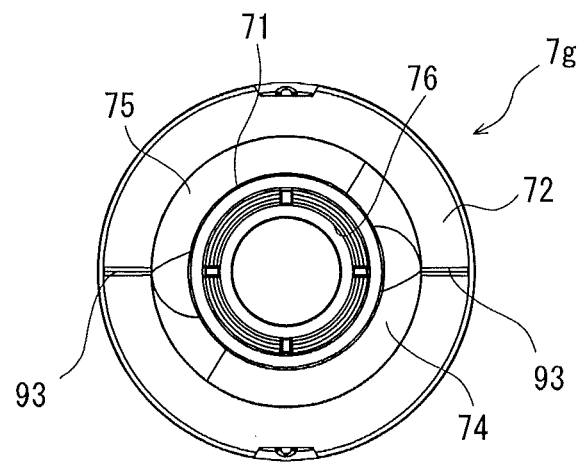
FIG. 45 is a plan view of the plunger-mounting member shown in FIG. 43.
Figure 48:
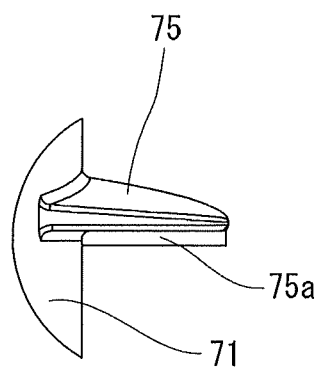
FIG. 48 is a partly enlarged view of FIG. 43.
Figure 49:
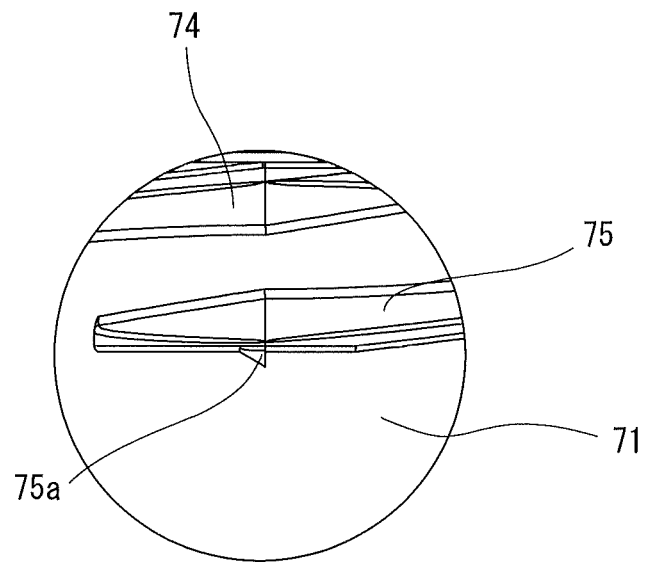
FIG. 49 is a partly enlarged view of FIG. 44.

It is preferable that the spiral ribs 74, 75 formed on the outer surfaces of the distal portions of the distal parts 71 of the plunger-mounting members of all of the above-described embodiments have the form in the end portion thereof as shown in FIG. 48 which is an enlarged view of the portion encircled with the round dashed line shown in FIGS. 42, 43, and 44 and the form in the end portion thereof as shown in FIG. 49 which is an enlarged view of the portion encircled with the round dashed line shown in FIG. 44.

As shown in FIGS. 42, 43, 44, 48, and 49, in the plunger-mounting member 7g of this embodiment, the spiral ribs 74, 75 have projected portions 74a, 75a respectively formed on the proximal end surface of the proximal portion thereof. The projected portions 74a, 75a are so formed as to be projected from the proximal end surfaces of the proximal portions of the spiral ribs 74, 75 respectively toward the disk-shaped distal side flange part 72 capable of pressing the proximal end surface of the gasket body 6. In mounting the plunger on the plunger-mounting member mounted on the proximal side of the gasket, in dependence on a mounting method, for example, in the case where the plunger is screwed on the plunger-mounting member without pressing the plunger against the plunger-mounting member and in the case where the plunger is screwed on the plunger-mounting member by inserting the plunger thereinto from below, a resisting force acting between the gasket and the plunger-mounting member can be smaller than a resisting force acting between the plunger-mounting member and the plunger. The projected portions 74a, 75a prevent the plunger-mounting member from idling with respect to the gasket with the plunger being held together with the plunger-mounting member and thus the work of mounting the plunger on the plunger-mounting member from being difficult. That is, the projected portions 74a, 75a formed on the proximal end surfaces of the proximal portions of the spiral ribs 74, 75 respectively have the function of preventing the plunger-mounting member from idling with respect to the gasket.

The projected portions 74a, 75a are formed at the proximal ends of the spiral ribs 74, 75 at positions distal from the proximal end thereof by a predetermined length. More specifically, each of the spiral ribs 74, 75 has an end portion not spiral but almost orthogonal to the axis of the plunger-mounting member 7g (the axis of the distal part 71) at the proximal portion thereof. The termination point of the end portion of each of the spiral ribs 74, 75 becomes gradually smaller toward the proximal end (termination point) thereof in its projected width (projected width with respect to the side surface of the distal part 71 of the plunger-mounting member 7g). In the plunger-mounting member 7g of this embodiment, the projected portions 74a, 75a are formed respectively on the end portions of the spiral ribs 74, 75 not spiral but almost orthogonal to the axis of the plunger-mounting member 7g (the axis of the distal part 71). In this embodiment, the projected portions 74a, 75a are formed at portions of the spiral ribs 74, 75 where a normal projected width thereof is maintained (portion where the widths of the spiral ribs 74, 75 are not decreased).

The projected height of the projected portions 74a, 75a with respect to the proximal end surface of the proximal portion of each of the spiral ribs 74, 75 is favorably 0.1 to 1 mm and more favorably 0.2 to 0.5 mm. It is preferable that the projected portions 74a, 75a have pointed apex portion (edge portion) respectively. It is preferable that the projected portions 74a, 75a are approximately triangular in the sections thereof. As shown in FIGS. 48 and 49, it is preferable that the angles of the projected portions 74a, 75a at the apex portions thereof are 15 to 60 degrees. When the angles of the projected portions 74a, 75a at the apex portions thereof are less than 15 degrees, they have a low strength and thus there is a fear that they may be broken. When the angles of the projected portions 74a, 75a at the apex portions thereof are more than 60 degrees, the amount of thrust of the apex portions thereof into the gasket is insufficient, thus, to allow the apex portions to cut sufficiently into the gasket, it is necessary to make the height of the projected portions large, bringing a fear that it is difficult to mount the plunger-mounting member on the gasket at a production time.

In the plunger-mounting member 7g of this embodiment, as described above, the ribs 93 are formed on the distal end surface of the distal side flange part 72. The projected portion 74a of the spiral rib 74 is so formed as to confront one of the ribs 93 formed on the distal side flange part 72 (specifically, the projected portion 74a of the spiral rib 74 is so formed as to axially confront one of the ribs 93, in other words, so formed as to position the projected portion 74a and one of the ribs 93 on the same straight line parallel with the axis of the plunger-mounting member 7g). Similarly the projected portion 75a of the spiral rib 75 is also so formed as to confront the other rib 93 formed on the distal side flange part 72 (specifically, the projected portion 75a of the spiral rib 75 is so formed as to axially confront the other rib 93, in other words, so formed as to position the projected portion 75a and the other rib 93 on the same straight line parallel with the axis of the plunger-mounting member 7g).

Figure 50:
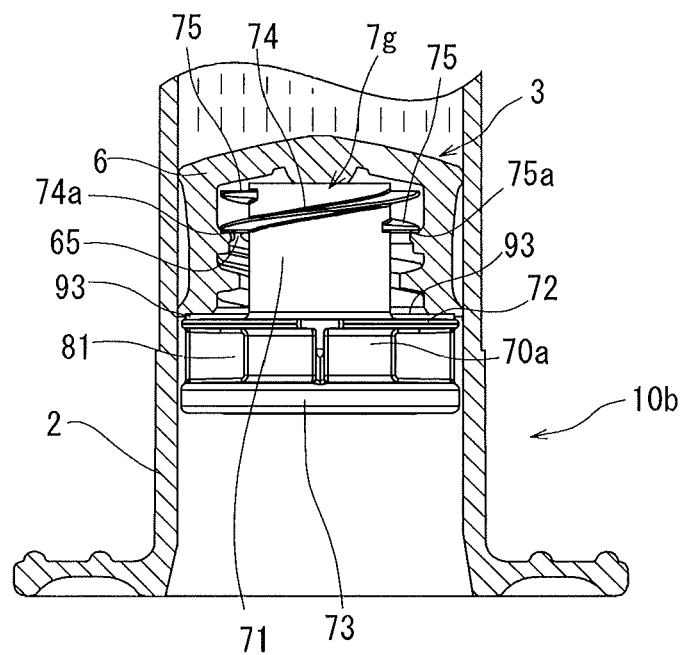
FIG. 50 is an explanatory view for explaining a state in which the plunger-mounting member, shown in FIG. 43, which is used for a prefilled syringe is mounted on a gasket.

As shown in FIG. 50, in the above-described construction, a prefilled syringe 10b using the plunger-mounting member 7g has a form in which the gasket body is sandwiched between the projected portion 74a of the spiral rib 74 and one of the ribs 93 of the distal side flange part 72. Similarly the prefilled syringe 10b has a form in which the gasket body is sandwiched between the projected portion 75a of the spiral rib 75 and the other rib 93 of the distal side flange part 72. Thereby the plunger-mounting member 7g can be securely prevented from idling with respect to the gasket body. In the prefilled syringe 10b of this embodiment, as shown in FIG. 50, the distal end (edge portion) of the projected portion 74a of the spiral rib 74 and the distal end (edge portion) of one of the ribs 93 of the distal side flange part 72 cut into the gasket body 6. Thereby it is possible to securely prevent the plunger-mounting member 7g from idling with respect to the gasket body 6.

In the prefilled syringe using the plunger-mounting member 7g of this embodiment, as shown in FIG. 50, similarly to the prefilled syringes 50 of the embodiment shown in FIGS. 23 and 29, the outer cylinder 2 accommodates the gasket 3 having the gasket body 6 on which the plunger-mounting member 7g is mounted. The proximal end of the plunger-mounting member 7g is not substantially projected beyond the proximal end of the outer cylinder 2, but is located at the position distal from the proximal end of the outer cylinder 2 by the predetermined length. The plunger-mounting member 7g is mounted on the gasket body 6, as described below.

After the spiral ribs 74, 75 of the plunger-mounting member 7g are inserted into the gasket body 6 from the start point of the spiral screwing part 63, the plunger-mounting member 7g is rotated. Thereby, screwing between the spiral screwing part 63 and the spiral ribs 74, 75 progresses. During the progress of the screwing therebetween, the start points of the spiral ribs 74, 75 of the plunger-mounting member 7g approach the termination point of the spiral screwing part 63 of the gasket body 6 and the rib-absent portion 65 of the annular projected part 64 thereof and are positioned between the spiral projection 66 forming the spiral screwing part 63 and the annular projected part 64. By further rotating the plunger-mounting member 7g, the spiral ribs 74, 75 pass the rib-absent portion 65 of the annular projected part 64 and enter the accommodation part 62. By continuing to rotate the plunger-mounting member 7g, as shown in FIG. 50, the spiral ribs 74, 75 entirely pass the rib-absent portion 65 of the annular projected part 64, and the portion of the distal part 71 of the plunger-mounting member 7g where the spiral ribs are formed is accommodated inside the accommodation part 62 of the gasket body 6. The distal end (edge portion) of the projected portion 74a of the spiral rib 74 and the distal end (edge portion) of one of the ribs 93 of the distal side flange part 72 cut into the gasket body 6 a little with the gasket body 6 being sandwiched between the projected portions 74a and 74a and between the two ribs 93 of the distal side flange part 72. Thereby the work of mounting the plunger-mounting member 7g on the gasket body 6 finishes.

The prefilled syringe of the present invention is as described below.

(1) The prefilled syringe comprising a prefilled syringe body including an outer cylinder, a gasket slidably accommodated inside the outer cylinder, a sealing member for sealing an opening formed at a distal end of the outer cylinder, and a medicine accommodated inside a medicine accommodation part formed inside the outer cylinder; and a plunger which can be mounted on the gasket and is not mounted thereon. The gasket is composed of a gasket body which is a tubular body whose distal end is closed and proximal end is open and has a lumen part extended from an opening formed at the proximal end thereof to a distal side thereof and a plunger-mounting member mounted on the gasket body. The plunger-mounting member has a body part which is a tubular body having a hollow part penetrating therethrough from one end thereof to other end thereof and has a distal side flange part capable of pressing a proximal end surface of the gasket body at a distal side thereof, a distal part which is projected distally from the body part and can be accommodated inside the lumen part of the gasket body, a spiral rib formed on an outer surface of the distal part, a proximal side flange part formed at a proximal side of the body part, and a plunger-mounting part, formed inside a proximal portion of the body part, on which the plunger is to be mounted. The gasket body has a spiral screwing part, formed on an inner surface of the lumen part, which is to screw the spiral rib of the plunger-mounting member and an accommodation part, disposed distally from the spiral screwing part of the lumen part, for accommodating a portion of the distal part of the plunger-mounting member where the spiral rib is formed. The plunger has a pressing part capable of pressing a proximal end surface of the proximal side flange part of the plunger-mounting member in mounting the plunger on the gasket and a mounting distal part, projected distally from the pressing part, which is capable of entering the plunger-mounting part of the plunger-mounting member. The plunger-mounting part of the plunger-mounting member has a spiral concave portion and an engaging rib located at a position in a vicinity of the spiral concave portion and distal therefrom. The mounting distal part of the plunger has a spiral projected portion capable of screwing the spiral concave portion of the plunger-mounting member and an engaging portion, disposed in vicinity of the spiral projected portion and at a distal side thereof, which engages the engaging rib of the plunger-mounting member. Then the plunger-mounting member is mounted on the gasket body, the spiral rib is received in the accommodation part of the gasket body and a distal end of the plunger-mounting member does not contact an inner surface of the gasket body; and when the plunger is mounted on the gasket, the mounting distal part of the plunger does not contact the inner surface of the gasket body.

In this prefilled syringe, similarly to ordinary prefilled syringes, the plunger can be mounted on the gasket by rotating the plunger. Therefore compared with a prefilled syringe adopting a concave-convex fit-on method, an operator does not have a sense of discomfort in the mounting operation. Further in the case of the prefilled syringe adopting the concave-convex fit-on method, the operator tends to strongly grasp the side of the outer cylinder to resist a shock which is generated at the time when the plunger and the gasket are fitted on each other, which causes the outer cylinder to deform and a liquid to leak. On the other hand, in the prefilled syringe of the present invention, liquid leak caused by the pressing of the outer cylinder during a work does not occur.

In the prefilled syringe of the invention of the present application, by inserting the mounting distal part of the plunger into the proximal portion of the plunger-mounting member with the plunger being rotated, it is possible to mount the plunger on the prefilled syringe body and confirm the engagement between the engaging portion of the plunger and the plunger-mounting part, when the engaging portion of the plunger and the plunger-mounting part have engaged each other in the plunger-mounting work. When the plunger mounted on the prefilled syringe body is rotated, the rotational force of the plunger is not transmitted to the gasket body, although the rotational force thereof is transmitted to the plunger-mounting member. Thus the gasket does not deform. The gasket body and the plunger-mounting member are fitted on each other in substantially a free fit-on state. Thus when the plunger is inclined, the gasket does not deform and thus liquid leak is unlikely to occur.

The embodiment of the prefilled syringe of the present invention may have a construction as follows:

(2) A prefilled syringe according to the above (1), wherein by inserting said mounting distal part of said plunger into a proximal portion of said plunger-mounting member and rotating said plunger, screwing between said spiral projected portion of said mounting distal part and said spiral concave portion of said plunger-mounting member progresses, and said engaging portion of said plunger proceeds and rides across said engaging rib of said plunger-mounting member, thus engaging said engaging rib.

(3) A prefilled syringe according to the above (1) or (2), wherein when said engaging portion of said plunger engages said engaging rib of said plunger-mounting member, said spiral projected portion of said plunger and said spiral concave portion of said plunger-mounting member engage each other.

(4) A prefilled syringe according to any one of the above (1) through (3), wherein said engaging portion of the plunger is constructed of a plurality of claw portions formed on said distal part of said plunger and convex portions formed on outer surfaces of said claw portions; and when said engaging portion of said plunger rides across said engaging rib of said plunger-mounting member, said convex portions engage said engaging rib.

(5) A prefilled syringe according to the above (4), wherein a plurality of said claw portions is disposed on substantially the same circumference.

(6) A prefilled syringe according to the above (4) or (5), wherein outer surfaces of said claw portions are formed as inclined surfaces which incline from distal ends of said claw portions to said convex portions.

(7) A prefilled syringe according to any one of the above (1) through (6), wherein said engaging rib of said plunger-mounting member is annular; and an inner surface of said engaging rib forms a tapered surface which tapers such that a diameter of said engaging rib becomes gradually smaller toward a distal end side of said plunger-mounting member.

(8) A prefilled syringe according to any one of the above (1) through (7), wherein said gasket body has an annular projected part, for preventing removal of said plunger therefrom, which is located at a position in a vicinity of said spiral screwing part and distal therefrom; and said annular projected part has a guide portion for guiding said spiral rib formed on said body part of said plunger-mounting member to said accommodation part, when said spiral rib reaches said annular projected part owing to progress of screwing between said spiral rib of said body part of said plunger-mounting member and said spiral screwing part of said gasket body.

(9) A prefilled syringe according to the above (8), wherein a rib of said annular projected part becomes gradually smaller toward said guide portion.

(10) A prefilled syringe according to any one of the above (1) through (9), wherein said spiral projected portion of said plunger mounting member is composed of two lines; and said spiral concave portion of said plunger is composed of two lines corresponding to said two lines of said spiral projected portion.

(11) A prefilled syringe according to any one of the above (1) through (10), wherein said plunger-mounting member has a projected portion which is formed on a proximal end surface of a proximal portion of said spiral rib and projected toward said distal side flange part thereof.

(12) A prefilled syringe according to any one of the above (1) through (11), wherein said plunger-mounting member has a rib formed on said distal side flange part thereof and is projected toward said spiral rib.

The detailed description above describes features and aspects of embodiments of a prefilled syringe disclosed by way of various examples. The invention is not limited, however, to the precise embodiments and variations described. Changes, modifications and equivalents can be employed by one skilled in the art without departing from the spirit and scope of the invention as defined in the appended claims. It is expressly intended that all such changes, modifications and equivalents which fall within the scope of the claims are embraced by the claims.

What is claimed is:

1. A prefilled syringe comprising:
    a prefilled syringe body including an outer cylinder, a gasket slidably accommodated inside the outer cylinder, a sealing member sealing an opening at the distal end of the outer cylinder, and medicine accommodated inside the outer cylinder;
    a plunger to be attached to the gasket at the time of use of the prefilled syringe;
    the gasket comprising a gasket body and a plunger-mounting member mounted on the gasket body,
    the gasket body possessing a closed distal end, an open proximal end and a lumen part provided in the gasket body, the gasket body including a spiral projection provided at a proximal portion of an inner surface of the gasket body;
    the plunger-mounting member comprising a body part, a distal side flange part provided at a distal portion of the body part and configured to press against a proximal end surface of the gasket body, a distal part projecting distally from the distal side flange part, a spiral rib provided on an outer surface of the distal part and adapted to the spiral projection of the gasket body, a proximal side flange part at a proximal end of the body part; and a plunger-mounting part inside a proximal portion of the body part;
    the lumen part of the gasket body including an accommodation part disposed distally from the spiral projection for accommodating a portion of the plunger-mounting member at which is located the spiral rib of the plunger-mounting member;
    the plunger including a pressing part for pressing a proximal end surface of the proximal side flange part of the plunger-mounting member, and a mounting distal part projecting distally from the pressing part and configured to enter the plunger-mounting part of the plunger-mounting member;
    the plunger-mounting part of the plunger-mounting member including an engaging rib and a spiral concave portion located between the proximal side flange part and the engaging rib;
    the mounting distal part of the plunger including an engaging portion which engages the engaging rib of the plunger-mounting member and a spiral projected portion configured to screw engage the spiral concave portion of the plunger-mounting member and located between the pressing part and the engaging portion;
    a distance between the proximal side flange part and a distal end of the engaging rib of the plunger-mounting member is approximately the same as a distance between the pressing part and a proximal end of the engaging portion of the plunger; and
    the mounting distal part of the plunger does not contact the inner surface of the gasket body when the plunger is attached to the gasket.

2. A prefilled syringe according to claim 1, wherein the plunger-mounting member includes a rib provided to the body part and located between the spiral rib and the distal side flange part and contacting the spiral projection of the gasket body.

3. A prefilled syringe according to claim 1, wherein the gasket body includes an annular projected part located between the accommodation part and the spiral projection, the annular projected part including a guide portion for guiding the spiral ribs of the plunger-mounting member to the accommodation part of the gasket body, and the plunger-mounting member includes a projected portion formed on a proximal end surface of the spiral rib and contacting to the annular projected part of the gasket body.

4. A prefilled syringe according to claim 3, wherein the distal side flange part of the plunger-mounting member includes a rib formed on a distal surface of the distal side flange part and contacting to the proximal end surface of the gasket body.

5. A prefilled syringe according to claim 1, wherein the gasket body includes an annular projected part located between the accommodation part and the spiral projection, the annular projected part including a guide portion for guiding the spiral ribs of the plunger-mounting member to the accommodation part of the gasket body, the plunger-mounting member including a projected portion formed on a proximal end surface of the spiral rib and contacting the annular projected part of the gasket body, and the plunger-mounting member possessing a form in which the gasket body is sandwiched between the projected portion of the spiral rib and the distal side flange part.

6. A prefilled syringe according to claim 1, wherein the gasket body includes an annular projected part located between the accommodation part and the spiral projection, the annular projected part includes a guide portion for guiding the spiral ribs of the plunger-mounting member to the accommodation part of the gasket body, the plunger-mounting member includes a projected portion formed on a proximal end surface of the spiral rib and contacting the annular projected part of the gasket body, the distal side flange part of the plunger-mounting member includes a rib formed on a distal surface of the distal side flange part and contacting to the proximal end surface of the gasket body, and the plunger-mounting member possessing a form in which the gasket body is sandwiched between the projected portion of the spiral rib and the ribs of the distal side flange part.

7. A prefilled syringe according to claim 1, wherein the portion of the distal part that includes the spiral rib of the plunger-mounting member is received in the accommodation part of the gasket body, and the gasket including a space between an inner surface of the closed distal end and a distal end of the distal part that includes the spiral rib of the plunger-mounting member; and the accommodation part without the spiral projection in the gasket body possessing an inner diameter greater than an outer diameter of the distal part that includes the spiral rib of the plunger-mounting member.

8. A prefilled syringe comprising:
a prefilled syringe body including an outer cylinder, a gasket slidably accommodated inside the outer cylinder, a sealing member sealing an opening at the distal end of the outer cylinder, and medicine accommodated inside the outer cylinder;
a plunger to be attached to the gasket at the time of use of the prefilled syringe;
the gasket comprising a gasket body and a plunger-mounting member mounted on the gasket body,
the gasket body possessing a closed distal end, an open proximal end and a lumen part provided in the gasket body, the gasket body including a spiral projection provided at a proximal portion of an inner surface of the gasket body;
the plunger-mounting member comprising a body part, a distal side flange part provided at a distal portion of the body part and configured to press a proximal end surface of the gasket body, a distal part projecting distally from the distal side flange part, a spiral rib provided on an outer surface of the distal part and adapting to the spiral projection of the gasket body, a proximal side flange part at a proximal end of the body part; and a plunger-mounting part inside a proximal portion of the body part;
the lumen part of the gasket body including an accommodation part disposed distally from the spiral projection for accommodating a portion that includes the spiral rib of the plunger-mounting member;
the plunger including a pressing part for pressing a proximal end surface of the proximal side flange part of the plunger-mounting member, and a mounting distal part projecting distally from the pressing part and configured to enter the plunger-mounting part of the plunger-mounting member;
the plunger-mounting part of the plunger-mounting member including an engaging rib and a spiral concave portion located between the proximal side flange part and the engaging rib;
the mounting distal part of the plunger including an engaging portion which engages the engaging rib of the plunger-mounting member and a spiral projected portion configured to screw engage the spiral concave portion of the plunger-mounting member and located between the pressing part and the engaging portion,
a distance between the proximal side flange part and a distal end of the engaging rib of the plunger-mounting member is approximately the same as a distance between the pressing part and a proximal end of the engaging portion of the plunger,
the portion of the distal part of the plunger-mounting member that includes the spiral rib is received in the accommodation part of the gasket body, and the gasket including a space between an inner surface of the closed distal end and a distal end of the distal part of the plunger-mounting member that includes the spiral rib; and the accommodation part without the spiral projection in the gasket body possessing an inner diameter greater than an outer diameter of the distal part of the plunger-mounting member that includes the spiral rib; and
the mounting distal part of the plunger does not contact the inner surface of the gasket body when the plunger is attached to the gasket.

9. A prefilled syringe comprising:
a prefilled syringe body including an outer cylinder, a gasket slidably accommodated inside the outer cylinder, a sealing member sealing an opening at the distal end of the outer cylinder, and medicine accommodated inside the outer cylinder;
a plunger to be attached to the gasket at the time of use of the prefilled syringe;
the gasket comprising a gasket body and a plunger-mounting member mounted on the gasket body,
the gasket body possessing a closed distal end, an open proximal end and a lumen part provided in the gasket body, the gasket body also including a spiral projection provided at a proximal portion of an inner surface of the gasket body;
the plunger-mounting member comprising a body part, a distal side flange part provided at a distal portion of the body part and configured to press a proximal end surface of the gasket body, a distal part projecting distally from the distal side flange part, a spiral rib provided on an outer surface of the distal part and adapting to the spiral projection of the gasket body, a proximal side flange part at a proximal end of the body part; and a plunger-mounting part inside a proximal portion of the body part;
the lumen part of the gasket body including an accommodation part disposed distally from the spiral projection for accommodating a portion that includes the spiral rib of the plunger-mounting member;
the plunger including a pressing part for pressing a proximal end surface of the proximal side flange part of the plunger-mounting member, and a mounting distal part projecting distally from the pressing part and configured to enter the plunger-mounting part of the plunger-mounting member;
the plunger-mounting part of the plunger-mounting member including an engaging rib and a spiral concave portion located between the proximal side flange part and the engaging rib;
the mounting distal part of the plunger including an engaging portion which engages the engaging rib of the plunger-mounting member and a spiral projected portion configured to screw engage the spiral concave portion of the plunger-mounting member and located between the pressing part and the engaging portion,
a distance between the proximal side flange part and a distal end of the engaging rib of the plunger-mounting member is approximately the same as a distance between the pressing part and a proximal end of the engaging portion of the plunger,
the mounting distal part of the plunger does not contact the inner surface of the gasket body when the plunger is attached to the gasket; and
the gasket body includes an annular projected part located between the accommodation part and the spiral projection, the annular projected part including a guide portion for guiding the spiral ribs of the plunger-mounting member to the accommodation part of the gasket body, the plunger-mounting member including a projected portion formed on a proximal end surface of the spiral rib and contacting the annular projected part of the gasket body, and the plunger-mounting member possessing a form in which the gasket body is sandwiched between the projected portion of the spiral rib and the distal side flange part.

10. A prefilled syringe according to claim 9, wherein the plunger-mounting member includes a rib formed on a distal surface of the distal side flange part and contacting to the proximal end surface of the gasket body, and the plunger-mounting member possesses a form in which the gasket body is sandwiched between the projected portion of the spiral rib and the ribs of the distal side flange part.

* * * * *